United States Patent
Bhatti et al.

(10) Patent No.: US 7,384,929 B2
(45) Date of Patent: Jun. 10, 2008

(54) N-ARYL AZASPIROALKENE AND AZASPIROALKANE COMPOUNDS AND METHODS OF PREPARATION AND USE THEREOF

(75) Inventors: Balwinder Bhatti, Winston-Salem, NC (US); Scott R. Breining, Winston-Salem, NC (US); Philip S. Hammond, Winston-Salem, NC (US); Jozef Klucik, Marietta, GA (US); Yun-De Xiao, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 297 days.

(21) Appl. No.: 11/230,140

(22) Filed: Sep. 19, 2005

(65) Prior Publication Data

US 2006/0074067 A1   Apr. 6, 2006

Related U.S. Application Data

(60) Provisional application No. 60/611,535, filed on Sep. 20, 2004.

(51) Int. Cl.
| | |
|---|---|
| A61K 31/397 | (2006.01) |
| A61K 33/4402 | (2006.01) |
| A61K 33/4406 | (2006.01) |
| A61K 33/4409 | (2006.01) |
| C07D 211/18 | (2006.01) |
| C07D 215/06 | (2006.01) |
| C07D 217/04 | (2006.01) |
| C07D 219/02 | (2006.01) |
| C07D 221/20 | (2006.01) |
| C07D 237/08 | (2006.01) |
| C07D 239/26 | (2006.01) |
| C07D 239/42 | (2006.01) |
| C07D 401/04 | (2006.01) |
| C07D 261/06 | (2006.01) |
| C07D 271/06 | (2006.01) |
| C07D 413/04 | (2006.01) |
| C07D 498/10 | (2006.01) |
| C07D 271/10 | (2006.01) |
| C07D 257/02 | (2006.01) |
| C07D 417/04 | (2006.01) |
| C07D 513/10 | (2006.01) |
| A61K 31/501 | (2006.01) |
| A61K 31/497 | (2006.01) |
| A61K 31/427 | (2006.01) |

(52) U.S. Cl. ............ 514/210.16; 514/278; 514/252.04; 514/255.04; 514/256; 514/364; 514/378; 514/372; 546/15; 546/16; 544/230; 548/247; 548/131; 548/143; 548/214

(58) Field of Classification Search .................. 546/15, 546/16; 514/210.16, 278
See application file for complete search history.

(56) References Cited

U.S. PATENT DOCUMENTS

| | | | | |
|---|---|---|---|---|
| 3,654,305 | A | * | 4/1972 | German ...................... 548/408 |
| 4,922,901 | A | | 5/1990 | Brooks et al. |
| 4,963,557 | A | * | 10/1990 | Badger et al. .............. 514/278 |
| 5,187,166 | A | | 2/1993 | Kikuchi et al. |
| 5,583,140 | A | | 12/1996 | Bencherif et al. |
| 5,597,919 | A | | 1/1997 | Dull et al. |
| 5,604,231 | A | | 2/1997 | Smith et al. |
| 5,616,716 | A | | 4/1997 | Dull et al. |
| 5,663,356 | A | | 9/1997 | Ruecroft et al. |
| 5,672,601 | A | | 9/1997 | Cignarella |
| 5,733,912 | A | | 3/1998 | Wasicak et al. |
| 5,852,041 | A | | 12/1998 | Cosford et al. |
| 6,022,868 | A | | 2/2000 | Olesen et al. |

(Continued)

FOREIGN PATENT DOCUMENTS

EP    0 297858 A2    1/1989

(Continued)

OTHER PUBLICATIONS

Badger, et al., J. Med. Chem. (1990), 33(11), 2963-70.*

(Continued)

*Primary Examiner*—Mark L. Berch
*Assistant Examiner*—Cecilia M Jaisle
(74) *Attorney, Agent, or Firm*—Womble Carlyle Sandridge & Rice, PLLC

(57) ABSTRACT

Compounds, pharmaceutical compositions including the compounds, and methods of preparation and use thereof are disclosed. The compounds are N-aryl or heteroaryl azaspiroalkene/alkane compounds, prodrugs or metabolites of these compounds, or pharmaceutically acceptable salts thereof. The aryl group can be a phenyl ring or a five- or six-membered heterocyclic ring (heteroaryl). The compounds and compositions can be used to treat and/or prevent a wide variety of conditions or disorders, particularly those disorders characterized by dysfunction of nicotinic cholinergic neurotransmission, including disorders involving neuromodulation of neurotransmitter release, such as dopamine release. CNS disorders, which are characterized by an alteration in normal neurotransmitter release, are another example of disorders that can be treated and/or prevented. The compounds and compositions can also be used to alleviate pain. The compounds can: (i) alter the number of nicotinic cholinergic receptors of the brain of the patient, (ii) exhibit neuroprotective effects and (iii) when employed in effective amounts, not result in appreciable adverse side effects (e.g., side effects such as significant increases in blood pressure and heart rate, significant negative effects upon the gastro-intestinal tract, and significant effects upon skeletal muscle).

20 Claims, No Drawings

U.S. PATENT DOCUMENTS

| | | | |
|---|---|---|---|
| 6,051,596 A * | 4/2000 | Badger | 514/409 |
| 6,638,925 B2 | 10/2003 | Czollner et al. | |
| 6,878,732 B2 * | 4/2005 | Wrobleski et al. | 514/385 |
| 6,890,936 B2 * | 5/2005 | Boyle et al. | 514/316 |
| 7,214,691 B2 * | 5/2007 | Wu et al. | 514/322 |
| 2005/0049269 A1 | 3/2005 | Wu et al. | |

FOREIGN PATENT DOCUMENTS

| | | |
|---|---|---|
| EP | 0 360 390 A1 | 3/1990 |
| EP | 0 621 267 A1 | 10/1994 |
| EP | 621267 A1 * | 10/1994 |
| GB | 2 295 387 A | 5/1996 |
| WO | WO 94/08992 A1 | 4/1994 |
| WO | WO 96/31475 A2 | 10/1996 |
| WO | WO 96/40682 A1 | 12/1996 |
| WO | WO 98/25619 A1 | 6/1998 |
| WO | WO 99/21834 | 5/1999 |
| WO | WO 00/73300 A1 | 12/2000 |
| WO | WO 2002072549 A1 * | 9/2002 |
| WO | WO 03/091220 A1 | 11/2003 |
| WO | WO 2004/005293 A2 | 1/2004 |

OTHER PUBLICATIONS

Bryce, et al., Tetrahedron (1988), 44(2), 599-612.*
Grogan, et al., J. Med. Chem. (1965), 8(1), 62-73.*
Rice, et al., J. Med. Chem. (1963), 6(4), 388-402.*
Americ, S., et al., "Cholinergic channel modulators as a novel therapeutic strategy for Alzheimer's disease," *Exp. Opin. Invest. Drugs*, 5(1): 79-100 (1996).
Americ, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).
Bannon, A.W., et al., "ABT-594[(R)-5-(2-azetidinylmethoxy)-2-chloropyridine]: A Novel, Orally Effective Antinociceptive Agent Acting via Neuronal Nicotinic Acetylcholine Receptors: II. In Vivo Characterization," *J. Pharmacol. Exp. Ther.*, 285(2): 787-794 (1998).
Bannon, A.W., et al., "Broad-Spectrum, Non-Opioid Analgesic Activity by Selective Modulation of Neuronal Nicotonic Acetylcholine Receptors," *Science*, 279: 77-80 (1998).
Bencherif M. and R.J. Lukas, "Differential Regulation of Nicotinic Acetylcholine Receptor Expression by Human TE671/RD Cells Following Second Messenger Modulation and Sodium Butyrate Treatments," *Mol. Cell. Neurosci.*, 2(1): 52-65 (1991).
Bencherif, M., and R.J. Lukas, "Ligand Binding and Functional Characterization of Muscarinic Acetylcholine Receptors on the TE671/RD Human Cell Line," *J. Pharmacol. Exp. Ther.*, 257(3): 946-953 (1991).
Bencherif, M., et al., "RJR-2403: A Nicotinic Agonist with CNS Selectivity I: In Vitro Characterization," *J. Pharmacol. Exper. Therapeutics*, 279(3): 1413-1421 (1996).
Brioni, J.D., et al., "The Pharmacology of (-)-Nicotine and Novel Cholinergic Channel Modulators," *Adv. Pharmacol.*, 37: 153-214 (1997).
Cheng, Y.C., and W.H. Prusoff, "Relationship Between the Inhibition Constant (KI) and the Concentration of Inhibitor which Causes 50 Per Cent inhibition (I50) of an Enzymatic Reaction," *Biochem. Pharmacol.*, 22(23): 3099-3108 (1973).
Chiari, A., et al., "Sex Differences in Cholinergic Analgesia I: A Supplemental Nicotinic Mechanism in Normal Females," *Anesthesiology*, 91(5): 1447-1454 (1999).
Comins, D.L., and M.O. Killpack, "Lithiation of Methoxypyridines Directed by α-Amino Alkoxides," *J. Org. Chem.*, 55(1): 69-73 (1990).
Culbertson, T.P., et al., "Quinolone Antibacterial Agents Substituted at the 7-Position with Spiroamines. Synthesis and Structure-Activity Relationships," *J. Med. Chem.*, 33(8): 2270-2275 (1990).
Damaj, M.I., et al., "Analgesic Activity of Metanicotine, A Selective Nicotinic Agonist," *Society for Neuroscience*, 23: 669 Abstract 266.9 (1997).

Damaj, M.I., et al., "The antinociceptive effects of α7 nicotinic agonists in an acute pain model," *Neuropharmacology*, 39: 2785-2791 (2000).
Damaj, M.I., et al., "Antinociceptive and Pharmacological Effects of Metanicotine, a Selective Nicotinic Agonist," *J. Pharmacol. Exp. Ther.*, 291(1): 390-398 (1999).
Davies, Andrew R.L., et al., "Characterisation of the binding of [$^3$H]methyllycaconitine: a new radioligand for labeling α7-type neuronal nicotinic acetylcholine receptors," *Neuropharmacol.*, 38: 679-690 (1999).
Decina, P., et al., "Cigarette Smoking and Neuroleptic-Induced Parkinsonism," *Biol. Psychiatry*, 28(6): 502-508 (1990).
Elliott, J.M., et al., "Serine Derived NK1 Antagonists 2: A Pharmacophore Model for Arylsulfonamide Binding," *Bioorg. Med. Chem. Lett.*, 8: 1851-1856 (1998).
Feldgus, S. and C. Landis, "Catalytic Enantioselective Hydrogenation of Alkenes," Chap. 5, pp. 107-135, in *Catalysis by Metal Complexes*, vol. 25 (Kluwer Academic Publishers, 2002).
Genin, M.J., et al., "Synthesis and Crystal Structure of a Peptidomimetic Containing the (R)-4.4-Spiro Lactam Type-II b-Turn Mimic," *J. Org. Chem.*, 58(8): 2334-2237 (1993).
Gibson, S. et al., "Principal Components Describing Biological Activities and Molecular Diversity of Heterocyclic Aromatic Ring Fragments," *J. Med. Chem.*, 39: 4065-4072 (1996).
Hall, G.H., and D.M. Turner, "Effects of Nicotine on the Release of $^3$H-Noradrenaline fron the Hypothalamus," *Biochemical Pharmacology*, 21: 1829-1838 (1972).
Hansch, C., et al., "The Parabolic Dependence of Drug Action upon Lipophilic Character as Revealed by a Study of Hypnotics," *J. Med. Chem.*, 11(1): 1-11 (1967).
Hansch, C., et al., "A Survey of Hammett Substituent Constants and Resonance and Field Parameters," *Chem. Rev.*, 91(2): 165-195 (1991).
Hamon, M., "Neuropharmacology of anxiety: perspectives and prospects," *TiPS*, 15: 36-39 (1994).
Harsing, Jr., et al., "Dopamine Efflux from Striatum After Chronic Nicotine: Evidence for Autoreceptor Desensitization," *J. Neurochem.*, 59(1): 48-54 (1992).
Hertog, H.J.D., et al., "The Directive Influence of the N-Oxide Group During the Nitration of Derivatives of Pyridine N-Oxide (IV) [1]) Nitration of 3-bromo-5methoxy- and 3,5-dimethoxy-pyridine-N-oxide[2])," *Recueil Trav. Chim. Pays-Bas.*, 74(8/9): 1171-1179 (1955).
Hery, F., et al. "Control of the Release of Newly Synthetized $^3$H-5-Hydroxytryptamine by Nicotinic and Muscarinic Receptors in Rat Hypothalamic Slices," *Naunyn-Schmiedeberg's Arch. Pharmacol.*, 296: 91-97 (1977).
Hinds, M.G., et al., "Synthesis, Conformational Properties, and Antibody Recoginition of Peptides Containing β-Turn Mimetics Based on a-Alkylproline Derivatives," *J. Med. Chem.*, 34(6): 1777-1789 (1991).
Hoffman, J.M., et al., "Synthesis and Evaluation of 2-Pyridinone Derivatives as HIV-1-Specific Reverse Transcriptase Inhibitors. 4. 3-[2-(Benzoxazol-2-yl)ethyl]-5-ethyl-6-methylpyridin-2(1H)-one and Analogues," *J. Med. Chem.*, 36(8): 953-966 (1993).
Holladay, M.W., et al., "Neuronal Nicotinic Acetylcholine Receptors as Targets for Drug Discovery," *J. Med. Chem.*, 40(26): 4169-4194 (1997).
Hoyer, D. and H.W.G.M. Boddeke, "Partial agonists, full agonists, antagonists: dilemmas of definition," *TiPS Reviews*, 14: 270-275 (1993).
Hughes, D.L., "The Mitsunobu Reaction," *Org. React.*, 42:335-657 (1992).
Hughes, D.L., "Progress in the Mitsunobu Reaction. A Review," *Org. Prep. Proced. Int.*, 28(1): 129-164 (1996).
Hughes, J., "S 40 Nicotine and Neuropsychiatric Disorders," Session 6, in *International Symposium on Nicotine: The Effects of Nicotine on Biological Systems II*, (Birkhäuser Verlag Publishers, 1994).
Kan, T., et al., "Sterocontrolled Total Synthesis of Potent Immunosuppressant FR9011483," *Org. Lett.*, 6(16):2729-2731 (2004).

Kim, K., et al., "Novel Bicyclic Lactams as XaaPro Type VI β Turn Mimics: Design, Synthesis and Evaluation," *J. Org. Chem.*, 61(9): 3138-3144 (1996).

Klingsberg, E., editor, "Pyridine and Its Derivatives," Part Three, pp. 3-5, in *Chemistry of Heterocyclic Compounds*, vol. 14 (Interscience Publishers, 1962).

Latli, B., et al., "Novel and Potent 6-Chloro-3-pyridinyl Ligands for the α4β2 Neuronal Nicotnic Acetylcholine Receptor," *J. Med. Chem.*, 42(12): 2227-2234 (1999).

Lavand'homme, P., and J.C. Eisenach, "Sex Differences in Cholinergic Analgesia II: Differing Mechanisms in Two Models of Allodynia," *Anesthesiology*, 91(5): 1455-1461 (1999).

Lippiello, P.M., et al., "RJR-2403: A Nicotinic Agonist with CNS Selectivity II. In Vivo Characterization," *J. P. E. T.*, 279(3): 1422-1429 (1996).

Lowry, O.H., et al., "Protein Measurement with the Folin Phenol Reagent," *J. Biol. Chem.*, 193: 265-275 (1951).

Lukas, R.J., and M.J. Cullen, "An Isotopic Rubidium Ion Efflux Assay for the Functional Characterization of Nicotinic Acetylcholine Receptors on Clonal Cell Lines," *Anal. Biochem.*, 175(1): 212-218 (1988).

Lukas, R.J., et al., "Characterization of Nicotinic Acetylcholine Receptors Expressed by Cells of the SH-SY5Y Human Neuroblastoma Clonal Line," *Molec. Cellular Neurosci.*, 4(1): 1-12 (1993).

Lukas, R.J., "Pharmacological Distinctions between Functional Nicotine Acetylcholine Receptors on the PC12 Rat Pheochromocytoma and the TE671 Human Medulloblastoma," *J. Pharmacol. Exp. Ther.*, 251(1): 175-182 (1989).

Luther, M.A., et al., "A Muscle Acetylcholine Receptor is Expressed in the Human Cerebellar Medulloblastoma Cell Line TE671," *J. Neursci.*, 9(3): 1082-1096 (1989).

Marks, M.J., et al., "Nicotinic Binding Sites in Rat and Mouse Brain: Comparison of Acetylcholine, Nicotine, and α-Bungarotoxin," *Mol. Pharmacol.*, 30(5): 427-436 (1986).

Onaivi, E.S., et al., "Chronic Nicotine Reverses Age-Associated Increases in Tail-Flick Latency and Anxiety in Rats," *Life Sciences*, 54(3): 193-202 (1993).

Oswald, R.E., et al., "Characterization of nicotinic acetylcholine receptor channels of the TE671 human medulloblastoma clonal line," *Neurosci. Lett.*, 96: 207-212 (1989).

Overman, L.E., and T. Osawa, "A Convenient Synthesis of 4-Unsubsittuted β-Lactams," *J. Am. Chem. Soc.*, 107: 1698-1701 (1985).

Overman, L.E., and R.M. Burk, "A Convenient Synthesis of Unsymmetrical Secondary Amines. In Situ Formation of Unstable Formaldehyde Imines." *Tetrahedron Letters*, 25(16): 1635-1638 (1984).

Pomerleau, O.F., et al., "The Effects of Cigarette Smoking on Pain and Anxiety," *Addictive Behaviors*, 9: 265-271 (1984).

Pullan, R.D., et al. "Transdermal Nicotine for Active Ulcerative Colitis," *New England J. Med.*, 330(12): 811-815 (1994).

Rapier, C., et al., "Stereoselective Nicotine-Induced Release of Dopamine from Striatal Synaptosomes: Concentration Dependence and Repetitive Stimulation," *J. Neurochem.*, 50(4): 1123-1130 (1988).

Rapier, C., et al., "Nicotinic Modulation of [$^3$H]Dopamine Release from Striatal Synaptosomes: Pharmacological Characterisation," *J. Neurochem.*, 54(3): 937-45 (1990).

Romano, C., and A. Goldstein, "Sterospecific Nicotine Receptors on Rat Brain Membranes," *Science*, 210(7): 647-650 (1980).

Rowell, P.P., and D.L. Winkler, "Nicotinic Stimulation of [$^3$H] Acetylcholine Release from Mouse Cerebral Cortical Synaptosomes," *J. Neurochem,*, 43(6): 1593-1598 (1984).

Sanberg, P.R., et al., "Nicotine Potentiation of Haloperidol-Induced Catalepsy: Striatal Mechanisms," *Pharmacol. Biochem. & Behavior*, 46: 303-307 (1993).

Sandor, N.T., et al. "Effect of nicotine on dopaminergic-cholinergic interaction in the striatum," *Brain Res.*, 567: 313-316 (1991).

Sjak-Shie, N.N., and E.M. Meyer, "Effects of chronic nicotine and pilocarpine administration on neocortocal neuronal density and [$^3$H]GABA uptake in nucleus basalis lesioned rats," *Brain Res.*, 624: 295-298 (1993).

Smith, P.W., et al., "New Spiropiperidines as Potent and Selective Non-Peptide Tachykinin $NK_2$ Receptor Antagonists," *J. Med. Chem.*, 38(19): 3772-3779 (1995).

Stratton, M.R., et al., "Characterization of the human cell line TE671," *Carcinogenesis*, 10(5): 899-905 (1989).

Süess, V.R., *Helv. Chim. Acta,*. 60: 1650-1656 (1977).

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tripathi, H.L., et al., "Nicotine-Induced Antinociception of Rats and Mice: Correlation with Nicotine Brain Levels," *J. Pharmacol. Exp. Ther.*, 221(1): 91-96 (1982).

Vizi, E.S., "Acetylcholine release from guinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?," *Pharmacopsychiat.*, 21: 302-303 (1988).

Wardrop, D.J., and W. Zhang, "N-Methoxy-N-acylnitrenium Ions: Application to the formal Synthesis of (+)-Desmethylamino FR901483," *Organic Letters*, 3(5): 2353-2356 (2001).

Whiting, P. J., et al., "Functional acetylcholine receptor in PC12 cells reacts with a monoclonal antibody to brain nicotinic receptors," *Nature*, 327:515-518 (1987).

Whiting, P.J., et al., "Expression of nicotinic acetylcholine receptor subtypes in brain and retina," *Brain Res Mol Brain Res.*, 10(1): 61-70 (1991).

Williams, M., et al., "Neuronal Nicotinic Acetylchoilne Receptors," *Drug News Perspec.*, 7(4): 205-223 (1994).

Zwart, C., and J.P. Wibaut, "Chemical Behaviour of 3-Aminopyridine and of 3,5-Diaminopyridine. Syntheses of (3-Pyridyl)-Pyrazolones," *Recueil Trav. Chim. Pays-Bas*, 74(8/9): 1062-1069 (1955).

International Search Report (PCT/US2005/033270, dated Jan. 20, 2006).

* cited by examiner

N-ARYL AZASPIROALKENE AND AZASPIROALKANE COMPOUNDS AND METHODS OF PREPARATION AND USE THEREOF

RELATED APPLICATIONS

This application claims benefit of U.S. Provisional Patent Application No. 60/611,535, filed Sep. 20, 2004, the contents of which are fully incorporated herein by reference.

FIELD OF THE INVENTION

The present invention relates to pharmaceutical compositions incorporating compounds capable of affecting nicotinic cholinergic receptors, for example, as modulators of specific nicotinic receptor subtypes. The present invention also relates to methods for treating a wide variety of conditions and disorders, particularly those associated with dysfunction of the central and autonomic nervous systems.

BACKGROUND OF THE INVENTION

Nicotine exhibits a variety of pharmacological effects (Pullan et al., *N. Engl. J. Med.* 330:811-815 (1994)), some of which are due to neurotransmitter release (See, for example, Sjak-shie et al., *Brain Res.* 624:295 (1993), where neuroprotective effects of nicotine are proposed). For example, acetylcholine, dopamine, norepinephrine, serotonin and glutamate are released by neurons upon administration of nicotine (Rowell et al., *J. Neurochem.* 43:1593 (1984); Rapier et al., *J. Neurochem.* 50:1123 (1988); Sandor et al., *Brain Res.* 567:313 (1991) and Vizi, Br. *J. Pharmacol.* 47:765 (1973), (Hall et al., *Biochem. Pharmacol.* 21:1829 (1972), (Hery et al., *Arch. Int. Pharmacodyn. Ther.* 296:91 (1977)), and Toth et al., *Neurochem Res.* 17:265 (1992)). Confirmatory reports and additional recent studies show that nicotine administration modulates glutamate, nitric oxide, GABA, takykinins, cytokines and peptides in the central nervous system (CNS) (reviewed in Brioni et al., *Adv. Pharmacol.* 37:153 (1997)). Nicotine also reportedly potentiates the pharmacological behavior of certain pharmaceutical compositions used to treat certain disorders. See, for example, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Various additional beneficial pharmacological effects of nicotine have been proposed. See, for example, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *J. Pharmacol. Exp. Ther.* 221:91(1982) and Hamon, *Trends in Pharmacol. Res.* 15:36 (1994).

In addition to nicotine itself, a variety of nicotinic compounds are purportedly useful for treating a wide variety of conditions and disorders. See, for example, Williams et al., *Drug News Perspec.* 7(4):205 (1994); Arneric et al., *CNS Drug Rev.* 1(1):1 (1995); Arneric et al., *Exp. Opin. Invest. Drugs* 5(1):79 (1996); Bencherif et al., *J. Pharmacol. Exp. Ther.* 279:1413 (1996); Lippiello et al., *J. Pharmacol. Exp. Ther.* 279:1422 (1996); Damaj et al., *Neuroscience* (1997) *J. Pharmacol. Exp. Ther.* 291:390 (1999); Chiari et al., *Anesthesiology* 91:1447 (1999); Lavand'homme and Eisenbach, *Anesthesiology* 91:1455 (1999); Holladay et al., *J. Med. ChemChem.* 40(28):4169 (1997); Bannon et al., *Science* 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al.

Nicotine and various nicotinic compounds are reportedly useful for treating a wide variety of CNS disorders. See, for example, U.S. Pat. No. 5,1871,166 to Kikuchi et al., U.S. Pat. No. 5,672,601 to Cignarella, PCT WO 99/21834 and PCT WO 97/40049, UK Patent Application GB 2295387 and European Patent Application 297,858. CNS disorders are a type of neurological disorder. They can be drug-induced; attributed to genetic predisposition, infection or trauma; or of unknown etiology. CNS disorders include neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Relatively common CNS disorders include pre-senile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

Pain can be classified in various ways and can be characterized by a variety of geneses and etiologies (e.g., inflammatory pain, neuropathic pain, chronic pain). Current pain therapy is dominated by two classes of drugs, the non-steriodal anti-inflammatory drugs (NSAIDs) and the opioids, both of which have significant therapeutic liabilities. Various compounds which target nAChRs have been shown to be effective in treating one or more kinds of pain in animal models. See for instance, Damaj et al., *J. Pharmacol. Exp. Ther.* 291:390 (1999); Damaj et al., *Neuropharmacology* 39:2785-2791 (2000); Chiari et al., *Anesthesiology* 91:1447 (1999); Lavand'homme and Eisenbach, *Anesthesiology* 91:1455 (1999); Holladay et al., *J. Med. Chem.* 40(28):4169 (1997); Bannon et al., *Science* 279: 77 (1998); and Bannon et al., *J Pharmacol Exp Ther.* 285:787-794 (1998). It would be beneficial to provide pain relief without the gastrointestinal liabilities of the NSAIDs or the abuse potential of the opioids.

A limitation of some nicotinic compounds is that they are associated with various undesirable side effects, for example, by stimulating muscle and ganglionic receptors. It would be desirable to have compounds, compositions and methods for treating pain and preventing and/or treating various conditions or disorders (e.g., CNS disorders), including alleviating the symptoms of these disorders, where the compounds exhibitnicotinic pharmacology with a beneficial effect (e.g., upon the functioning of the CNS), but without significant associated side effects. It would further be highly desirable to provide compounds, compositions and methods that effect CNS function without significantly effecting those receptor subtypes which have the potential to induce undesirable side effects (e.g., appreciable activity at cardiovascular and skeletal muscle sites). The present invention provides such compounds, compositions and methods.

SUMMARY OF THE INVENTION

Compounds, pharmaceutical compositions including the compounds, and methods of preparation and use thereof are disclosed. The compounds are N-aryl azaspiroalkene and azaspiroalkane compounds, prodrugs or metabolites of these compounds, and pharmaceutically acceptable salts thereof. The aryl group can be a five- or six-membered heterocyclic ring (heteroaryl). Examples of the N-aryl azaspiroalkene/alkane compounds include 1-aza-8-(3-pyridinyl)spiro[4.5]dec-7-ene, 1-aza-8-(5-isopropoxy-3-pyridinyl)spiro[4.5]dec-7-ene, and N-methyl-1-aza-8-(5-isopropoxy-3-pyridinyl)spiro[4.5]dec-7-ene, and pharmaceutically acceptable salts thereof.

The compounds and compositions can be used to treat and/or prevent a wide variety of conditions or disorders, particularly those disorders characterized by dysfunction of nicotinic cholinergic neurotransmission, including disorders involving neuromodulation of neurotransmitter release, such as dopamine release. CNS disorders, which are characterized by an alteration in normal neurotransmitter release, are another example of disorders that can be treated and/or prevented. The compounds and compositions can also be used to alleviate pain. The methods involve administering to a subject an effective amount of an N-aryl azaspiroalkene/alkane compound or prodrug or metabolite thereof to alleviate the particular disorder.

The pharmaceutical compositions include an effective amount of the compounds described herein. When employed in effective amounts, the compounds can interact with relevant nicotinic receptor sites of a subject and act as a therapeutic agent to prevent and/or treat a wide variety of conditions and disorders, particularly those disorders characterized by an alteration in normal neurotransmitter release. The pharmaceutical compositions provide therapeutic benefit to individuals suffering from such disorders and exhibiting clinical manifestations of such disorders. When employed in effective amounts, the compounds have the potential to: (i) exhibit nicotinic pharmacology and affect relevant nicotinic receptors sites (e.g., bind to nicotinic acetylcholine receptors and modulate their function), and/or (ii) modulate neurotransmitter secretion and thus prevent and suppress the symptoms associated with those diseases. In addition, the compounds can: (i) alter the number of nicotinic cholinergic receptors of the brain of the patient, (ii) exhibit neuroprotective effects and (iii) when employed in effective amounts, not result in appreciable adverse side effects (e.g., side effects such as significant increases in blood pressure and heart rate, significant negative effects upon the gastro-intestinal tract, and significant effects upon skeletal muscle). The pharmaceutical compositions are believed to be safe and effective with regards to prevention and treatment of a wide variety of conditions and disorders. In one embodiment, the compositions are used to treat drug addiction and/or obesity.

The foregoing and other aspects of the present invention are explained in detail in the detailed description and examples set forth below.

DETAILED DESCRIPTION OF THE INVENTION

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched alkyl radicals including $C_1$-$C_8$, preferably $C_1$-$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity.

As used herein, a "partial antagonist" is a substance that provides a level of inhibition to its binding partner that is intermediate between that of a full or complete antagonist and an inactive ligand.

It will be recognized that stimulation, and hence, inhibition is defined intrinsically for any substance or category of substances to be defined as agonists, antagonists, or partial agonists. As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., *Trends Pharmacol Sci.* 14(7):270-5 (1993). Where such contextually specific evaluations are relevant, and how they might be relevant in the context of the present invention, will be apparent to one of ordinary skill in the art.

The term "modulation" includes full and partial activation and inhibition.

As used herein, neurotransmitters whose release is mediated by the compounds described herein include, but are not limited to, acetylcholine, dopamine, norepinephrine, serotonin, and glutamate, and the compounds described herein function as modulators at one or more of the Central Nervous System (CNS) nAChRs.

I. Compounds

The compounds are N-aryl or heteroaryl azaspiroalkene/alkane compounds, prodrugs or metabolites of these compounds, and pharmaceutically acceptable salts thereof.

The compounds can bind to, and modulate nicotinic acetylcholine receptors in the patient's brain in the cortex, hippocampus, thalamus, basal ganglia, and spinal cord. When so bound, the compounds express nicotinic pharmacology and, in particular, modulate the release of various neurotransmitters including dopamine, other catecholamines such as norepinephrine, such as serotonin, acetylcholine, GABA, glutamate, neuropeptides, nitric oxide, cytokines and other neurotransmitters and neuromediators. The compounds have a high affinity for the $\alpha_4\beta_2$ receptor.

Receptor binding constants provide a measure of the ability of the compound to bind to half of the relevant receptor sites of certain brain cells of the patient. See, for example, Cheng et al., *Biochem. Pharmacol.* 22:3099 (1973). The receptor binding constants of the compounds described herein generally exceed about 0.1 nM, often exceed about 1 nM, and frequently exceed about 10 nM, and are often less than about 100 μM, often less than about 10 μM and frequently less than about 5 μM. Preferred compounds generally have receptor binding constanta less than about 2.5 μM, sometimes are less than about 1 μM, and can be less than about 100 nM.

The compounds described herein can demonstrate a nicotinic function by effectively activating neurotransmitter secretion from nerve ending preparations (i.e., synaptosomes). As such, these compounds can activate relevant neurons to release or secrete acetylcholine, dopamine, and other neurotransmitters. Generally, typical compounds activate dopamine secretion in amounts of at least one third, typically at least about 10 times less, frequently at least about 100 times less, and sometimes at least about 1,000 times less than those required for activation of muscle-type nicotinic receptors. Certain compounds elicit dopamine secretion in an amount which is comparable to that elicited by an equal molar amount of (S)-(−)-nicotine.

Preferably, the compounds can cross the blood-brain barrier, and thus enter the central nervous system of the patient. Log P values provide a measure of the ability of a compound to pass across a diffusion barrier, such as a biological membrane, including the blood brain barrier. See, for example, Hansch et al., *J. Med. Chem.* 11:1 (1968). Typical log P values for the compounds described herein are generally greater than about −0.5, often are greater than about 0, and frequently are greater than about 0.5, and are typically less than about 3, often are less than about 2, and frequently are less than about 1.

In one embodiment, the compounds have the structure represented by Formula 1 below:

Formula I

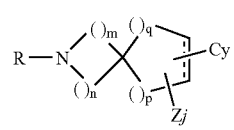

In the formula, R is H or $C_{1\text{-}10}$ alkyl, Cy is aryl or heteroaryl, the dashed line represents a carbon-carbon single or double bond, m=1, 2, 3 or 4, n=0, 1, or 2, p=0, 1, 2, or 3, q=0, 1, 2, 3, or 4, and j=0, 1, 2, or 3 non-hydrogen substituents (Z), with the proviso that when m is 1, n cannot be 0. The values of m, n, p and 1 are selected such that the azaspiroalkene/alkane ring contains 6, 7, 8, 9, 10 or 11 members, preferably 7, 8, 9 or 10 members.

In one embodiment, the values of m, n, p and q are selected, and the dashed line is selected, such that the azaspiroalkene/alkane ring is an azaspiro[3,4]octene, an azaspiro[4,4]-nonene, or an azaspiro[4,5]-decene. In another embodiment, the values of m, n, p and q are selected, and the dashed line is selected, such that the azaspiroalkene/alkane ring is a azaspiro[2,3]hexane, an azaspiro[2,4]heptane, an azaspiro[3,4]octane, an azaspiro[4,4]-nonane, or an azaspiro [4,5]-decane.

Each individual Z represents a suitable non-hydrogen substituent species (e.g., alkyl, substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl; but preferably lower alkyl or aryl).

In either formula, Cy represents a suitable five- or six-membered heteroaromatic ring. In one embodiment, Cy is a six membered ring of the formula:

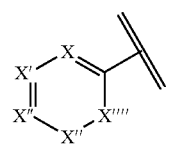

Each of X, X', X", X''' and X'''' is individually nitrogen, nitrogen bonded to oxygen (e.g., an N-oxide or N—O functionality) or carbon bonded to a substituent species. No more than three of X, X', X", X''' and X'''' are nitrogen or nitrogen bonded to oxygen, and it is preferred that only one or two of X, X', X", X''' and X'''' be nitrogen or nitrogen bonded to oxygen. In addition, it is highly preferred that not more than one of X, X', X", X''' and X'''' be nitrogen bonded to oxygen; and it is preferred that if one of those species is nitrogen bonded to oxygen, that species is X'''. Most preferably, X''' is nitrogen. In certain preferred circumstances, both X' and X''' are nitrogen. Typically, X, X" and X'''' are carbon bonded to a substituent species, and it is typical that the substituent species at X, X" and X'''' are hydrogen. In another embodiment, all of X, X', X", X''' and X'''' are carbon bonded to a substituent species (hydrogen or non-hydrogen). For certain other preferred compounds where X''' is carbon bonded to a substituent species such as hydrogen, X and X" are both nitrogen. In certain other preferred compounds where X' is carbon bonded to a substituent species such as hydrogen, X and X"' are both nitrogen.

In another embodiment, Cy is a five 5-membered heteroaromatic ring, such as pyrrole, furan, thiophene, isoxazole, isothiazole, oxazole, thiazole, pyrazole, 1,2,4-oxadiazole, 1,3,4-oxadiazole and 1,2,4-triazole. Other examples of such rings are described in U.S. Pat. No. 6,022,868 to Olesen et al., the contents of which are incorporated herein by reference in their entirety. One way of depicting Cy is as follows:

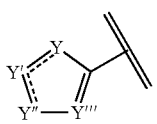

where Y and Y" are individually nitrogen, nitrogen bonded to a substituent species, oxygen, sulfur or carbon bonded to a substituent species, and Y' and Y"' are nitrogen or carbon bonded to a substituent species. The dashed lines indicate that the bonds (between Y and Y' and between Y' and Y") can be either single or double bonds. However, when the bond between Y and Y' is a single bond, the bond between Y' and Y" must be a double bond and vice versa. In cases in which Y or Y" is oxygen or sulfur, only one of Y and Y" is either oxygen or sulfur. At least one of Y, Y', Y" and Y"' must be oxygen, sulfur, nitrogen or nitrogen bonded to a substituent species. It is preferred that no more than three of Y, Y', Y" and Y"' be oxygen, sulfur, nitrogen or nitrogen bonded to a substituent species. It is further preferred that at least one, but no more than three, of Y, Y', Y" and Y"' be nitrogen.

Substituent species associated with any of X, X', X", X"', X"", Y, Y', Y" and Y"' (when any is carbon bonded to a substituent species or nitrogen bonded to a substituent species), typically have a sigma m value between about −0.3 and about 0.75, frequently between about −0.25 and about 0.6; and each sigma m value individually can be 0 or not equal to zero; as determined in accordance with Hansch et al., *Chem. Rev.* 91:165 (1991).

Examples of suitable substituent species associated with any of X, X', X", X"', X"", Y, Y', Y" and Y"' (when any is carbon bonded to a substituent species or nitrogen bonded to a substituent species), include hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR"R", —NR'C(=O)OR",       —SO$_2$R',       —SO$_2$NR'R",       and —NR'SO$_2$R", where R' and R" are individually hydrogen, lower alkyl (e.g., straight chain or branched alkyl including C$_1$-C$_8$, preferably C$_1$-C$_5$, such as methyl, ethyl, or isopropyl), cycloalkyl, heterocyclyl, aryl, or arylalkyl (such as benzyl), and r is an integer from 1 to 6. R' and R" can combine to form a cyclic functionality. The term "substituted" as applied to alkyl, aryl, cycloalkyl and the like refers to the substituents described above, starting with halo and ending with —NR'SO$_2$R".

Examples of suitable Cy groups include 3-pyridinyl (unsubstituted or substituted in the 5 and/or 6 position(s) with any of the aforementioned substituents), 5-pyrimidinyl (unsubstituted or substituted in the 2 position with any of the aforementioned substituents), 4 and 5-isoxazolyl, 4 and 5-isothiazolyl, 5-oxazolyl, 5-thiazolyl, 5-(1,2,4-oxadiazolyl), 2-(1,3,4-oxadiazolyl) or 3-(1,2,4-triazolyl).

Representative aryl groups include phenyl, naphthyl, furanyl, thienyl, pyridinyl, pyrimidinyl, pyrazinyl, pyridazinyl, quinolinyl, and indolyl. Other representative aromatic ring systems are set forth in Gibson et al., *J. Med. Chem.* 39:4065 (1996). Any of these aromatic group containing species can be substituted with at least one substituent group, such as those described above that are associated with x' and the like. Representative substitevely include alkyl, aryl, halo, hydroxy, alkoxy, aryloxy or amino substituents.

Adjacent substituents of X, X', X", X"', X"", Y, Y', Y" and Y"' (when substituents are present) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities.

Representative compounds within the scope of Formula 1 include the following:

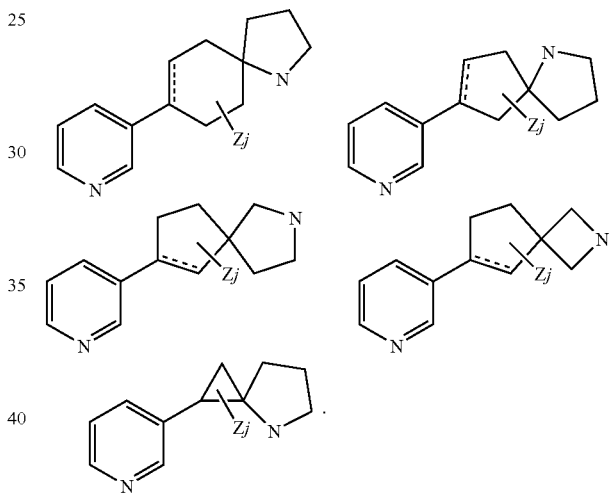

The compounds can occur in stereoisomeric forms, including both single enantiomers and racemic mixtures of such compounds, as well as mixtures of varying degrees of enantiomeric excess. Compounds of the present invention can, in some cases, occur as diastereomers, and each of the diasteromers is considered within the scope of the invention.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components. Representative salts are provided as described in U.S. Pat. No. 5,597,919 to Dull et al., U.S. Pat. No. 5,616,716 to Dull et al. and U.S. Pat. No. 5,663,356 to Ruecroft et al., the disclosures of which are incorporated herein by reference in their entirety.

Representative compounds include the following:
1-(3-pyridinyl)-5-azaspiro[2.3]hexane,
1-(5-methoxy-3-pyridinyl)-5-azaspiro[2.3]hexane,
1-(5-isopropoxy-3-pyridinyl)-5-azaspiro[2.3]hexane,
1-(5-cyclopentyloxy-3-pyridinyl)-5-azaspiro[2.3]hexane,
1-(5-phenoxy-3-pyiridinyl)-5-azaspiro[2.3]hexane,
1-(5-(4-chlorophenoxy)-3-pyridinyl)-5-azaspiro[2.3]hexane,
1-(5-bromo-3-pyridinyl)-5-azaspiro[2.3]hexane,
1-(5-cyano-3-pyridinyl)-5-azaspiro[2.3]hexane,
1-(6-chloro-3-pyridinyl)-5-azaspiro[2.3]hexane,
1-(6-hydroxy-3-pyridinyl)-5-azaspiro[2.3]hexane,
1-(6-methoxy-3-pyridinyl)-5-azaspiro[2.3]hexane,
1-(5-pyrimidinyl)-5-azaspiro[2.3]hexane,
1-(5-isoxazolyl)-5-azaspiro[2.3]hexane,
1-(5-isothiazolyl)-5-azaspiro[2.3]hexane,
1-(5-(1,2,4-oxadiazol)yl)-5-azaspiro[2.3]hexane,
1-(2-(1,3,4-oxadiazol)yl)-5-azaspiro[2.3]hexane,
1-(2-pyrazinyl)-5-azaspiro[2.3]hexane,
1-(3-pyridazinyl)-5-azaspiro[2.3]hexane,
1-(3-pyridinyl)-4-azaspiro[2.4]heptane,
1-(5-methoxy-3-pyridinyl)-4-azaspiro[2.4]heptane,
1-(5-isopropoxy-3-pyridinyl)-4-azaspiro[2.4]heptane,
1-(5-cyclopentyloxy-3-pyridinyl)-4-azaspiro[2.4]heptane,
1-(5-phenoxy-3-pyridinyl)-4-azaspiro[2.4]heptane,
1-(5-(4-chlorophenoxy)-3-pyridinyl)-4-azaspiro[2.4]heptane,
1-(5-bromo-3-pyridinyl)-4-azaspiro[2.4]heptane,
1-(5-cyano-3-pyridinyl)-4-azaspiro[2.4]heptane,
1-(6-chloro-3-pyridinyl)-4-azaspiro[2.4]heptane,
1-(6-hydroxy-3-pyridinyl)-4-azaspiro[2.4]heptane,
1-(6-methoxy-3-pyridinyl)-4-azaspiro[2.4]heptane,
1-(5-pyrimidinyl)-4-azaspiro[2.4]heptane,
1-(5-isoxazolyl)-4-azaspiro[2.4]heptane,
1-(5-isothiazolyl)-4-azaspiro[2.4]heptane,
1-(5-(1,2,4-oxadiazol)yl)-4-azaspiro[2.4]heptane,
1-(2-(1,3,4-oxadiazol)yl)-4-azaspiro[2.4]heptane,
1-(2-pyrazinyl)-4-azaspiro[2.4]heptane,
1-(3-pyridazinyl)-4-azaspiro[2.4]heptane,
2-(3-pyridinyl)-5-azaspiro[3.4]octane,
2-(5-methoxy-3-pyridinyl)-5-azaspiro[3.4]octane,
2-(5-isopropoxy-3-pyridinyl)-5-azaspiro[3.4]octane,
2-(5-cyclopentyloxy-3-pyridinyl)-5-azaspiro[3.4]octane,
2-(5-phenoxy-3-pyridinyl)-5-azaspiro[3.4]octane,
2-(5-(4-chlorophenoxy)-3-pyridinyl)-5-azaspiro[3.4]octane,
2-(5-bromo-3-pyridinyl)-5-azaspiro[3.4]octane,
2-(5-cyano-3-pyridinyl)-5-azaspiro[3.4]octane,
2-(6-chloro-3-pyridinyl)-5-azaspiro[3.4]octane,
2-(6-hydroxy-3-pyridinyl)-5-azaspiro[3.4]octane,
2-(6-methoxy-3-pyridinyl)-5-azaspiro[3.4]octane,
2-(5-pyrimidinyl)-5-azaspiro[3.4]octane,
2-(5-isoxazolyl)-5-azaspiro[3.4]octane,
2-(5-isothiazolyl)-5-azaspiro[3.4]octane,
2-(5-(1,2,4-oxadiazol)yl)-5-azaspiro[3.4]octane,
2-(2-(1,3,4-oxadiazol)yl)-5-azaspiro[3.4]octane,
2-(2-pyrazinyl)-5-azaspiro[3.4]octane,
2-(3-pyridazinyl)-5-azaspiro[3.4]octane,
6-(3-pyridinyl)-2-azaspiro[3.4]octane,
6-(5-methoxy-3-pyridinyl)-2-azaspiro[3.4]octane,
6-(5-isopropoxy-3-pyridinyl)-2-azaspiro[3.4]octane,
6-(5-cyclopentyloxy-3-pyridinyl)-2-azaspiro[3.4]octane,
6-(5-phenoxy-3-pyridinyl)-2-azaspiro[3.4]octane,
6-(5-(4-chlorophenoxy)-3-pyridinyl)-2-azaspiro[3.4]octane,
6-(5-bromo-3-pyridinyl)-2-azaspiro[3.4]octane,
6-(5-cyano-3-pyridinyl)-2-azaspiro[3.4]octane,
6-(6-chloro-3-pyridinyl)-2-azaspiro[3.4]octane,
6-(6-hydroxy-3-pyridinyl)-2-azaspiro[3.4]octane,
6-(6-methoxy-3-pyridinyl)-2-azaspiro[3.4]octane,
6-(5-pyrimidinyl)-2-azaspiro[3.4]octane,
6-(5-isoxazolyl)-2-azaspiro[3.4]octane,
6-(5-isothiazolyl)-2-azaspiro[3.4]octane,
6-(5-(1,2,4-oxadiazol)yl)-2-azaspiro[3.4]octane,
6-(2-(1,3,4-oxadiazol)yl)-2-azaspiro[3.4]octane,
6-(2-pyrazinyl)-2-azaspiro[3.4]octane,
6-(3-pyridazinyl)-2-azaspiro[3.4]octane,
7-(3-pyridinyl)-2-azaspiro[4.4]nonane,
7-(5-methoxy-3-pyridinyl)-2-azaspiro[4.4]nonane,
7-(5-isopropoxy-3-pyridinyl)-2-azaspiro[4.4]nonane,
7-(5-cyclopentyloxy-3-pyridinyl)-2-azaspiro[4.4]nonane,
7-(5-phenoxy-3-pyridinyl)-2-azaspiro[4.4]nonane,
7-(5-(4-chlorophenoxy)-3-pyridinyl)-2-azaspiro[4.4]nonane,
7-(5-bromo-3-pyridinyl)-2-azaspiro[4.4]nonane,
7-(5-cyano-3-pyridinyl)-2-azaspiro[4.4]nonane,
7-(6-cbloro-3-pyridinyl)-2-azaspiro[4.4]nonane,
7-(6-hydroxy-3-pyridinyl)-2-azaspiro[4.4]nonane,
7-(6-methoxy-3-pyridinyl)-2-azaspiro[4.4]nonane,
7-(5-pyrimidinyl)-2-azaspiro[4.4]nonane,
7-(5-isoxazolyl)-2-azaspiro[4.4]nonane,
7-(5-isothiazolyl)-2-azaspiro[4.4]nonane,
7-(5-(1,2,4-oxadiazol)yl)-2-azaspiro[4.4]nonane,
7-(2-(1,3,4-oxadiazol)yl)-2-azaspiro[4.4]nonane,
7-(2-pyrazinyl)-2-azaspiro[4.4]nonane,
7-(3-pyridazinyl)-2-azaspiro[4.4]nonane,
7-(3-pyridinyl)-1-azaspiro[4.4]nonane,
7-(5-methoxy-3-pyridinyl)-1-azaspiro[4.4]nonane,
7-(5-isopropoxy-3-pyridinyl)-1-azaspiro[4.4]nonane,
7-(5-cyclopentyloxy-3-pyridinyl)-1-azaspiro[4.4]nonane,
7-(5-phenoxy-3-pyridinyl)-1-azaspiro[4.4]nonane,
7-(5-(4-chlorophenoxy)-3-pyridinyl)-1-azaspiro[4.4]nonane,
7-(5-bromo-3-pyridinyl)-1-azaspiro[4.4]nonane,
7-(5-cyano-3-pyridinyl)-1-azaspiro[4.4]nonane,
7-(6-chloro-3-pyridinyl)-1-azaspiro[4.4]nonane,
7-(6-hydroxy-3-pyridinyl)-1-azaspiro[4.4]nonane,
7-(6-methoxy-3-pyridinyl)-1-azaspiro[4.4]nonane,
7-(5-pyrimidinyl)-1-azaspiro[4.4]nonane,
7-(5-isoxazolyl)-1-azaspiro[4.4]nonane,
7-(5-isothiazolyl)-1-azaspiro[4.4]nonane,
7-(5-(1,2,4-oxadiazol)yl)-1-azaspiro[4.4]nonane,
7-(2-(1,3,4-oxadiazol)yl)-1-azaspiro[4.4]nonane,
7-(2-pyrazinyl)-1-azaspiro[4.4]nonane,
7-(3-pyridazinyl)-1-azaspiro[4.4]nonane,
8-(3-pyridinyl)-1-azaspiro[4.5]decane,
8-(5-methoxy-3-pyridinyl)-1-azaspiro[4.5]decane,
8-(5-isopropoxy-3-pyridinyl)-1-azaspiro[4.5]decane,
8-(5-cyclopentyloxy-3-pyridinyl)-1-azaspiro[4.5]decane,
8-(5-phenoxy-3-pyridinyl)-1-azaspiro[4.5]decane,
8-(5-(4-chlorophenoxy)-3-pyridinyl)-1-azaspiro[4.5]decane,
8-(5-bromo-3-pyridinyl)-1-azaspiro[4.5]decane,
8-(5-cyano-3-pyridinyl)-1-azaspiro[4.5]decane,
8-(6-chloro-3-pyridinyl)-1-azaspiro[4.5]decane,
8-(6-hydroxy-3-pyridinyl)-1-azaspiro[4.5]decane,
8-(6-methoxy-3-pyridinyl)-1-azaspiro[4.5]decane,
8-(5-pyrimidinyl)-1-azaspiro[4.5]decane,
8-(5-isoxazolyl)-1-azaspiro[4.5]decane,
8-(5-isothiazolyl)-1-azaspiro[4.5]decane,
8-(5-(1,2,4-oxadiazol)yl)-1-azaspiro[4.5]decane,
8-(2-(1,3,4-oxadiazol)yl)-1-azaspiro[4.5]decane, 8-(2-pyrazinyl)-1-azaspiro[4.5]decane,
8-(3-pyridazinyl)-1-azaspiro[4.5]decane,
2-(3-pyridinyl)-7-azaspiro[4.5]decane,
2-(5-methoxy-3-pyridinyl)-7-azaspiro[4.5]decane,
2-(5-isopropoxy-3-pyridinyl)-7-azaspiro[4.5]decane,
2-(5-cyclopentyloxy-3-pyridinyl)-7-azaspiro[4.5]decane,
2-(5-phenoxy-3-pyridinyl)-7-azaspiro[4.5]decane,
2-(5-(4-chlorophenoxy)-3-pyridinyl)-7-azaspiro[4.5]decane,
2-(5-bromo-3-pyridinyl)-7-azaspiro[4.5]decane,
2-(5-cyano-3-pyridinyl)-7-azaspiro[4.5]decane,
2-(6-chloro-3-pyridinyl)-7-azaspiro[4.5]decane,
2-(6-hydroxy-3-pyridinyl)-7-azaspiro[4.5]decane,
2-(6-methoxy-3-pyridinyl)-7-azaspiro[4.5]decane,
2-(5-pyrimidinyl)-7-azaspiro[4.5]decane,
2-(5-isoxazolyl)-7-azaspiro[4.5]decane,
2-(5-isothiazolyl)-7-azaspiro[4.5]decane,
2-(5-(1,2,4-oxadiazol)yl)-7-azaspiro[4.5]decane,
2-(2-(1,3,4-oxadiazol)yl)-7-azaspiro[4.5]decane,
2-(2-pyrazinyl)-7-azaspiro[4.5]decane
and 2-(3-pyridazinyl)-7-azaspiro[4.5 ]decane.

The following are also representative compounds of the present invention:
6-(3-pyridinyl)-2-azaspiro[3.4]oct-5-ene,
6-(5-methoxy-3-pyridinyl)-2-azaspiro[3.4]oct-5-ene,
6-(5-isopropoxy-3-pyridinyl)-2-azaspiro[3.4]oct-5-ene,
6-(5-cyclopentyloxy-3-pyridinyl)-2-azaspiro[3.4]oct-5-ene,
6-(5-phenoxy-3-pyridinyl)-2-azaspiro[3.4]oct-5-ene,
6-(5-(4-chlorophenoxy)-3-pyridinyl)-2-azaspiro[3.4]oct-5-ene,
6-(5-bromo-3-pyridinyl)-2-azaspiro[3.4]oct-5-ene,
6-(5-cyano-3-pyridinyl)-2-azaspiro[3.4]oct-5-ene,
6-(6-chloro-3-pyridinyl)-2-azaspiro[3.4]oct-5-ene,
6-(6-hydroxy-3-pyridinyl)-2-azaspiro[3.4]oct-5-ene,
6-(6-methoxy-3-pyridinyl)-2-azaspiro[3.4]oct-5-ene,
6-(5-pyrimidinyl)-2-azaspiro[3.4]oct-5-ene,
6-(5-isoxazolyl)-2-azaspiro[3.4]oct-5-ene,
6-(5-isothiazolyl)-2-azaspiro[3.4]oct-5-ene,
6-(5-(1,2,4-oxadiazol)yl)-2-azaspiro[3.4]oct-5-ene,
6-(2-(1,3,4-oxadiazol)yl)-2-azaspiro[3.4]oct-5-ene,
6-(2-pyrazinyl)-2-azaspiro[3.4]oct-5-ene,
6-(3-pyridazinyl)-2-azaspiro[3.4]oct-5-ene,
7-(3-pyridinyl)-2-azaspiro[4.4]non-6-ene,
7-(5-methoxy-3-pyridinyl)-2-azaspiro[4.4]non-6-ene,
7-(5-isopropoxy-3-pyridinyl)-2-azaspiro[4.4]non-6-ene,
7-(5-cyclopentyloxy-3-pyridinyl)-2-azaspiro[4.4]non-6-ene,
7-(5-phenoxy-3-pyridinyl)-2-azaspiro[4.4]non-6-ene,
7-(5-(4-chlorophenoxy)-3-pyridinyl)-2-azaspiro[4.4]non-6-ene,
7-(5-bromo-3-pyridinyl)-2-azaspiro[4.4]non-6-ene,
7-(5-cyano-3-pyridinyl)-2-azaspiro[4.4]non-6-ene,
7-(6-chloro-3-pyridinyl)-2-azaspiro[4.4]non-6-ene,
7-(6-hydroxy-3-pyridinyl)-2-azaspiro[4.4]non-6-ene,
7-(6-methoxy-3-pyridinyl)-2-azaspiro[4.4]non-6-ene,
7-(5-pyrimidinyl)-2-azaspiro[4.4]non-6-ene,
7-(5-isoxazolyl)-2-azaspiro[4.4]non-6-ene,
7-(5-isothiazolyl)-2-azaspiro[4.4]non-6-ene,
7-(5-(1,2,4-oxadiazol)yl)-2-azaspiro[4.4]non-6-ene,
7-(2-(1,3,4-oxadiazol)yl)-2-azaspiro[4.4]non-6-ene,
7-(2-pyrazinyl)-2-azaspiro[4.4]non-6-ene,
7-(3-pyridazinyl)-2-azaspiro[4.4]non-6-ene,
7-(3-pyridinyl)-1-azaspiro[4.4]non-7-ene,
7-(5-methoxy-3-pyridinyl)-1-azaspiro[4.4]non-7-ene,
7-(5-isopropoxy-3-pyridinyl)-1-azaspiro[4.4]non-7-ene,
7-(5-cyclopentyloxy-3-pyridinyl)-1-azaspiro[4.4]non-7-ene,
7-(5-phenoxy-3-pyridinyl)-1-azaspiro[4.4]non-7-ene,
7-(5-(4-chlorophenoxy)-3-pyridinyl)-1-azaspiro[4.4]non-7-ene,
7-(5-bromo-3-pyridinyl)-1-azaspiro[4.4]non-7-ene,
7-(5-cyano-3-pyridinyl)-1-azaspiro[4.4]non-7-ene,
7-(6-chloro-3-pyridinyl)-1-azaspiro[4.4]non-7-ene,
7-(6-hydroxy-3-pyridinyl)-1-azaspiro[4.4]non-7-ene,
7-(6-methoxy-3-pyridinyl)-1-azaspiro[4.4]non-7-ene,
7-(5-pyrimidinyl)-1-azaspiro[4.4]non-7-ene,
7-(5-isoxazolyl)-1-azaspiro[4.4]non-7-ene,
7-(5-isothiazolyl)-1-azaspiro[4.4]non-7-ene,
7-(5-(1,2,4-oxadiazol)yl)-1-azaspiro[4.4]non-7-ene,
7-(2-(1,3,4-oxadiazol)yl)-1-azaspiro[4.4]non-7-ene,
7-(2-pyrazinyl)-1-azaspiro[4.4]non-7-ene,
7-(3-pyridazinyl)-1-azaspiro[4.4]non-7-ene,
8-(3-pyridinyl)-1-azaspiro[4.5]dec-7-ene,
8-(5-methoxy-3-pyridinyl)-1-azaspiro[4.5]dec-7-ene,
8-(5-isopropoxy-3-pyridinyl)-1-azaspiro[4.5]dec-7-ene,
8-(5-cyclopentyloxy-3-pyridinyl)-1-azaspiro[4.5]dec-7-ene,
8-(5-phenoxy-3-pyridinyl)-1-azaspiro[4.5]dec-7-ene,
8-(5-(4-chlorophenoxy)-3-pyridinyl)-1-azaspiro[4.5]dec-7-ene,
8-(5-bromo-3-pyridinyl)-1-azaspiro[4.5]dec-7-ene,
8-(5-cyano-3-pyridinyl)-1-azaspiro[4.5]dec-7-ene,
8-(6-chloro-3-pyridinyl)-1-azaspiro[4.5]dec-7-ene,
8-(6-hydroxy-3-pyridinyl)-1-azaspiro[4.5]dec-7-ene,
8-(6-methoxy-3-pyridinyl)-1-azaspiro[4.5]dec-7-ene,
8-(5-pyrimidinyl)-1-azaspiro[4.5]dec-7-ene,
8-(5-isoxazolyl)-1-azaspiro[4.5]dec-7-ene,
8-(5-isothiazolyl)-1-azaspiro[4.5]dec-7-ene,
8-(5-(1,2,4-oxadiazol)yl)-1-azaspiro[4.5]dec-7-ene,
8-(2-(1,3,4-oxadiazol)yl)-1-azaspiro[4.5]dec-7-ene,
8-(2-pyrazinyl)-1-azaspiro[4.5]dec-7-ene,
8-(3-pyridazinyl)-1-azaspiro[4.5]dec-7-ene,
2-(3-pyridinyl)-7-azaspiro[4.5]dec-1-ene,
2-(5-methoxy-3-pyridinyl)-7-azaspiro[4.5]dec-1-ene,
2-(5-isopropoxy-3-pyridinyl)-7-azaspiro[4.5]dec-1-ene,
2-(5-cyclopentyloxy-3-pyridinyl)-7-azaspiro[4.5]dec-1-ene,
2-(5-phenoxy-3-pyridinyl)-7-azaspiro[4.5]dec-1-ene,
2-(5-(4-chlorophenoxy)-3-pyridinyl)-7-azaspiro[4.5]dec-1-ene,
2-(5-bromo-3-pyridinyl)-7-azaspiro[4.5]dec-1-ene,
2-(5-cyano-3-pyridinyl)-7-azaspiro[4.5]dec-1-ene,
2-(6-chloro-3-pyridinyl)-7-azaspiro[4.5]dec-1-ene,
2-(6-hydroxy-3-pyridinyl)-7-azaspiro[4.5]dec-1-ene,
2-(6-methoxy-3-pyridinyl)-7-azaspiro[4.5]dec-1-ene,
2-(5-pyrimidinyl)-7-azaspiro[4.5]dec-1-ene,
2-(5-isoxazolyl)-7-azaspiro[4.5]dec-1-ene,
2-(5-isothiazolyl)-7-azaspiro[4.5]dec-1-ene,
2-(5-(1,2,4-oxadiazol)yl)-7-azaspiro[4.5 ]dec-1-ene,
2-(2-(1,3,4-oxadiazol)yl)-7-azaspiro[4.5]dec-1-ene,
2-(2-pyrazinyl)-7-azaspiro[4.5]dec-1-ene,
and 2-(3-pyridazinyl)-7-azaspiro[4.5]dec-1-ene II. Methods of Preparing the Compounds The compounds of Formula 1 can be prepared using a general method involving reacting an aryl or heteroaryl Grignard or organolithium compound with a carbonyl group in a pre-formed azaspiroalkanone compound. The resulting intermediate includes a hydroxy group at a position adjacent to the aryl/heteroaryl ring, and this hydroxy group can be eliminated to form a double bond (or, in the case of asymmetric compounds, two different regioisomeric double bonds, which can be separated via chromatography or other means). If the saturated compound is desired, the double bond can be hydrogenated using known chemistry.

The azaspiroalkanone compounds can be prepared in a variety of methods. One such method is exemplified below in Scheme I, using 1-azaspiro[4.5]decan-2,8-dione ethylene ketal (described by Wardrop and Zhang, *Org. Lett.* 3(15): 2353-2356 (2001) and Kan et al., *Org. Lett.* 6(16): 2729-2731 (2004)) as a starting material. The amide group can be reduced to an amine, for example, using lithium aluminum hydride. The resulting amine group can be protected, for example, using ethyl chloroformate, and the ketal can be hydrolyzed to give a ketone functionality. The ketone can be reacted with an aryl or heteroaryl Grignard or organolithium compound, to form an intermediate including a hydroxy group on the same carbon as the aryl or heteroaryl ring. This tertiary alcohol can then be dehydrated to form an alkene (for example, by reaction with an acid, such as concentrated formic acid). The amine can then be deprotected. Scheme I is shown below:

Landis, *Catalysis by Metal Complexes*, 25:107-135 (2002), the contents of which are hereby incorporated by reference.

Modification of the Aryl/Heteroaryl Ring

Although a 3-lithiopyridine is added to the ketone ("oxo") group in the chemistry described in Scheme I, other aryl and heteroaryl rings are known to form Grignard and/or organolithium reagents, any of which can be used in the above chemistry. Examples include phenylmagnesium bromide, 5-lithiopyrimidine, and the like. These rings can be formed, for example, by appropriate reaction of a halogenated aryl or heteroaryl ring with magnesium, or by metal/halogen exchange with another organolithium reagent, such as n-butyllithium. The aryl or heteroaryl rings can be functionalized with virtually any substituent that does not interfere with the formation of a Grignard or organolithium reagent. Examples include ethers, thioethers, protected hydroxy groups, protected amine groups, protected thiols, ketals, acetals,

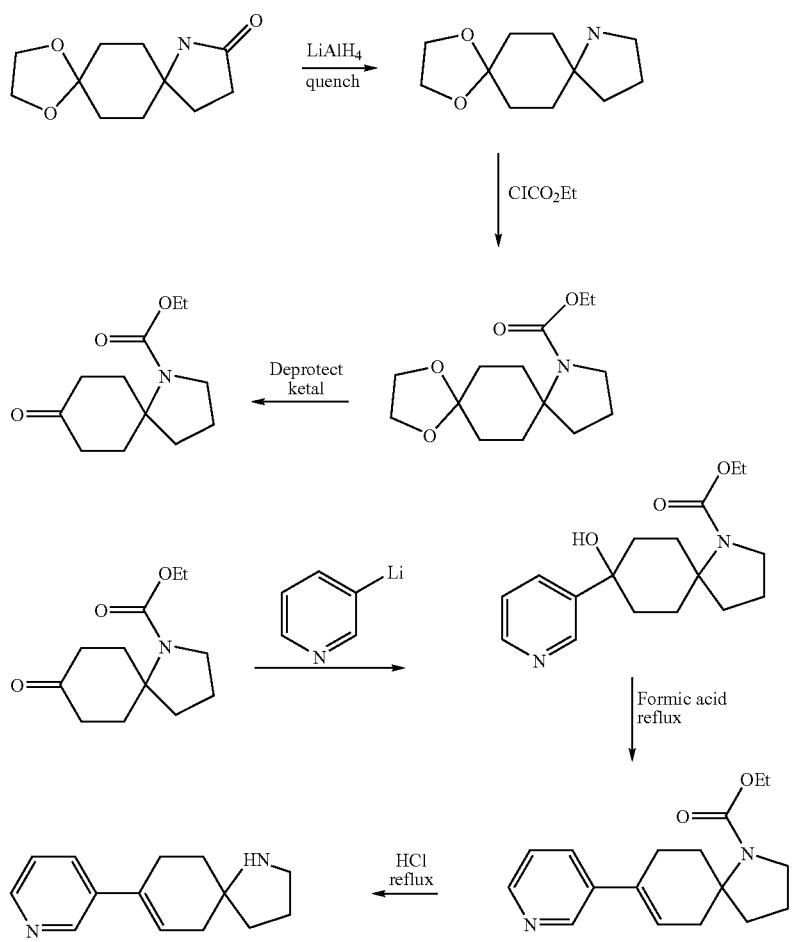

Formation of Azaspiroalkanes

Azaspiroalkanes can be prepared from the corresponding azaspiroalkenes by simply reducing the double bond in the latter compound, for example, using hydrogen and a palladium catalyst. If desired, one can form an enantiomerically enriched compound by known conditions for catalytic hydrogenation (see, for example, "Catalytic enantioselective hydrogenation of alkenes," Steven Feldgus and Clark R.

amides, alkyl groups, alkenyl groups, alkynyl groups, aryl groups, heteroaryl groups, heterocyclic groups, and the like.

Less reactive halogens can be present, in addition to a more reactive halogen used to prepare the organolithium or Grignard reagent, where the more reactive halogen is used to form the Grignard/organolithium reagent. After the coupling step, the remaining halogen can either be retained, or used to provide additional modification to the compound.

Where protected groups are used (i.e., for hydroxy, amine, thiol, ketone and aldehyde groups), the groups can be deprotected after the coupling reaction is complete. As with the less reactive halogens described above, these groups can either be retained, or used to provide additional modification to the compound.

A number of other analogs, bearing substituents in the 5 position of the pyridine ring, can be synthesized from the corresponding amino compounds, vide supra, via a 5-diazonium salt intermediate. Examples of other 5-substituted analogs that can be produced from 5-diazonium salt intermediates include, but are not limited to: 5-hydroxy, 5-alkoxy, 5-fluoro, 5-chloro, 5-iodo, 5-cyano, and 5-mercapto. These compounds can be synthesized using the general techniques set forth in Zwart et al., supra. For example, 5-hydroxy substituents can be prepared from the reaction of the corresponding 5-diazonium salt intermediate with water. Likewise, 5-alkoxy substituents can be prepared by reacting the diazonium salt with alcohols. Appropriate 5-diazonium salts can be used to synthesize cyano or halo compounds, as will be known to those skilled in the art. 5-Mercapto substitutions can be obtained using techniques described in Hoffman et al., *J. Med. Chem.* 36: 953 (1993). The 5-mercaptan so generated can, in turn, be converted to a 5-alkylthio substitutent by reaction with sodium hydride and an appropriate alkyl bromide. Subsequent oxidation would then provide a sulfone. 5-Acylamido analogs of the aforementioned compounds can be prepared by reaction of the corresponding 5-amino compounds with an appropriate acid anhydride or acid chloride using techniques known to those skilled in the art of organic synthesis.

5-Hydroxy-substituted analogs of the aforementioned compounds can be used to prepare corresponding 5-alkanoyloxy-substituted compounds by reaction with the appropriate acid, acid chloride, or acid anhydride. Likewise, the 5-hydroxy compounds are precursors of both the 5-aryloxy and 5-heteroaryloxy via nucleophilic aromatic substitution at electron deficient aromatic rings (e.g., 4-fluorobenzonitrile and 2,4-dichloropyrimidine). Such chemistry is well known to those skilled in the art of organic synthesis. Ether derivatives can also be prepared from the 5-hydroxy compounds by alkylation with alkyl halides and a suitable base or via Mitsunobu chemistry, in which a trialkyl- or triarylphosphine and diethyl azodicarboxylate are typically used. See Hughes, *Org. React.* (N.Y.) 42: 335 (1992) and Hughes, *Org. Prep. Proced. Int.* 28: 127 (1996) for typical Mitsunobu conditions.

Chemistries analogous to those described hereinbefore for the preparation of 5-substituted pyridine analogs of azaspiro compounds can be devised for the synthesis of analogs bearing substituents in the 2, 4, and 6 positions of the pyridine ring. For example, a number of 2-, 4-, and 6-aminopyridyl azaspiroalkanes can be converted to the corresponding diazonium salt intermediates, which can be transformed to a variety of compounds with substituents at the 2, 4, and 6 positions of the pyridine ring as was described for the 5-substituted analogs above. The requisite 2-, 4-, and 6-aminopyridyl azaspiroalkanes are available via the Chichibabin reaction of unsubstituted pyridyl azaspiroalkanes with sodium amide. Similar reactions are described in *Chemistry of Heterocyclic Compounds*, Volume 14, part 3, pp. 3-5 (Interscience Publishers, 1962) and by Lahti et al., *J. Med. Chem.* 42: 2227 (1999).

After the desired heteroaryl ring functional group manipulation has been accomplished, the optional protecting group can be removed from the azabicycle using appropriate conditions. Those skilled in the art of organic chemistry will appreciate the necessity of pairing protecting groups with the chemistries required to generate particular functionalities. In some cases it can be necessary, to retain a particular functionality, to replace one protecting group with another.

One method for introducing functionality to the pyridine rings is to start with a compound such as 3,5-dibromopyridine, and convert it to the corresponding 5-alkoxy-3-bromo- and 5-aryloxy-3-bromopyridines by the action of sodium alkoxides or sodium aryloxides. Procedures such as those described by Comins et al., *J. Org. Chem.* 55: 69 (1990) and Hertog et al., *Recueil Trav. Chim. Pays-Bas* 74: 1171 (1955) are used. Reaction of 3,5-dibromopyridine with sodium 4-methoxyphenoxide in N,N-dimethylformamide gives 3-bromo-5-(4-methoxyphenoxy)pyridine. The bromo group can be used to form an appropriate Grignard or organolithium reagent, and used in the coupling chemistry described above.

Formation of Different Ring Systems

One can readily prepare azaspiro compounds with different sized rings by starting with oxo-protected alkyl cycloalkane carboxylates with 3-7 carbons in the cycloalkane ring. Also, one can prepare compounds that include substitution at any position, provided the substituents either do not interfere with the chemistry, or are protected until such interfering steps have already been performed.

Several methods can be used to form the azaspiro ring systems, where the ring nitrogen is present at either the 1 or 2-position. For example, commercially available cyclopentane rings including a ketal group and an carboalkoxy group are known, and others can be synthesized using known methods. Examples include ethyl 2-oxocyclopentanecarboxylate, ethyl 3-oxocyclopentanecarboxylate, ethyl 2-oxocyclohexanecarboxylate, ethyl 3-oxocyclohexanecarboxylate, and ethyl 4-oxocyclohexanecarboxylate, all of which are all commercailly available.

In the case of the 2-oxo starting materials, the ketone and ester groups are positioned such that deprotonation and subsequent alkylation is relatively simple, and the deprotonation occurs primarily in the desired position (at the carbon between the ketone and ester groups) so it can be advantageous to alkylate (for example, with bromoacetonitrile) first and then protect the ketone as a ketal for subsequent steps. Where the oxo group is present at other than the 2-position, deprotonation could occur alpha to the ketone or the ester group, so it is advantageous to protect the oxo (ketone) group before the deprotonation/alkylation step.

The alkylation chemistry can be used to incorporate a sidechain that includes appropriate substitution to permit, in a series of subsequent steps, the cyclization to form the azaspiro ring system. Once the ring system is formed, the ketal can be deprotected. The resulting ketone can be reacted with an appropriate reagent to incorporate the aryl/heteroaryl ring. The arylation can be done either by a) an addition reaction involving an aryl or heteroaryl Grignard or organolithium reagent and the ketone, followed by dehydration of the resulting hydroxy group, or b) by enol triflate formation and subsequent Suzuki coupling of an aryl or heteroaryl ring to the enol triflate.

Representative reaction schemes for forming the azaspiro ring systems from the cyclopentane rings including alkyl carboxylate and protected-oxo groups are shown below.

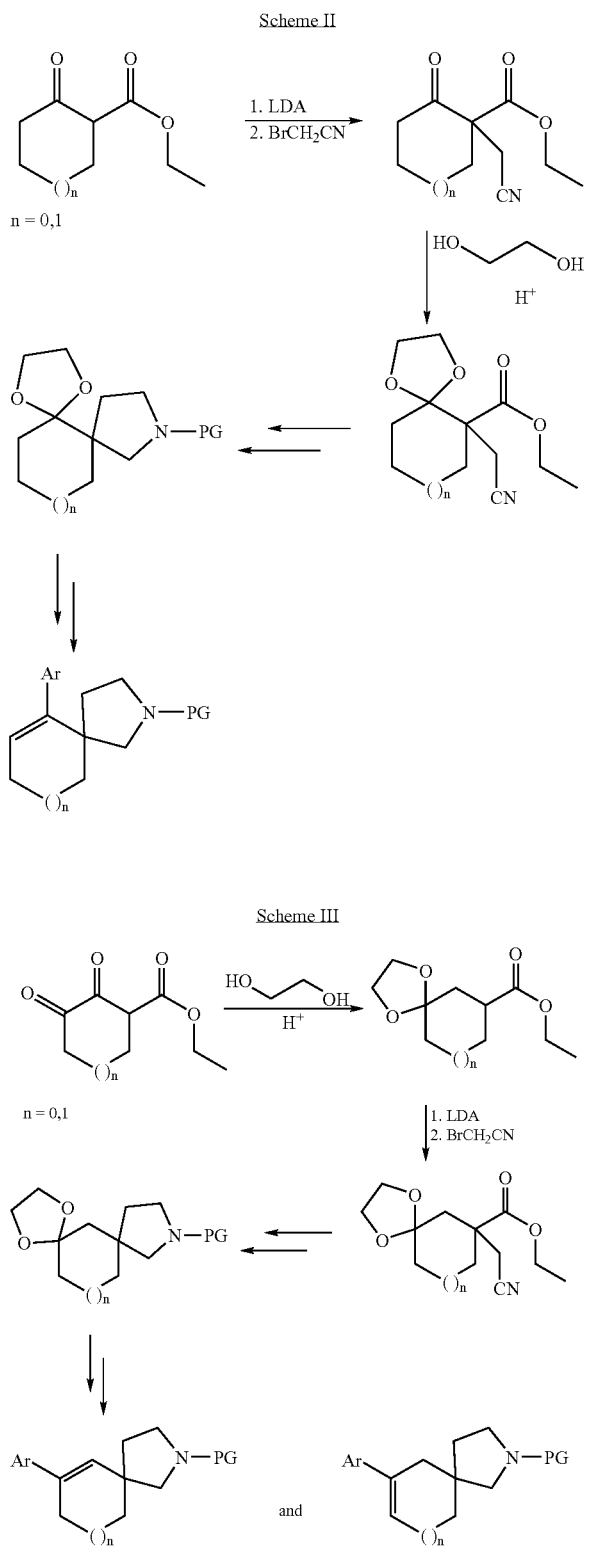

In Scheme II, a cyclopentane ethyl ester with a suitably protected oxo group at the 2-position is first deprotonated and alkylated, and the oxo group is then protected (in one embodiment, as a ketal group). In Scheme III, a cyclopentane ethyl ester with a suitably protected oxo group at the 3-position is first protected, then the position alpha to the ester group is deprotonated and alkylated.

Alkylation can be performed in one embodiment by using a strong base such as lithium diisopropylamide (LDA) and the aminomethyl equivalent cyanomethylbenzylamine, which provides a beta-lactam (this is a modification of the procedure reported by Overman, J. Am. Chem. Soc. 107: 1698 (1985) and Tet. Lett. 25:1635 (1985)). The resulting intermediate can subsequently be reduced with lithium aluminum hydride to provide the N-benzyl-2-azaspiro[3,4] octane, containing a protected ketone functionality. Deprotection of the ketone, subsequent coupling with the appropriate Grignard or organolithium reagent, and dehydration of the resulting alcohol, will provide the desired aza-protected azaspiroalkene compounds. Removal of the benzyl protecting group, by oxidative cleavage with, for example, ceric ammonium nitrate, will produce the desired 2-azaspiro[3,4]octene. Reduction of the double bond will form the desired azaspiroalkane.

The compounds of Formula 1 which possess the 2-azaspiro[4.4]nonane system can be prepared according to numerous methods. In one embodiment, an ethyl cyclopentanecarboxylate (which also includes a suitably protected ketone functionality) can be deprotonated with LDA and allowed to react by Michael addition to nitroethylene. Subsequent reduction of the nitro group using Raney nickel, followed by lactamization by methods known to those skilled in the art (for example, heating in a suitable solvent with or without an acidic or basic catalyst), provides 2-azaspiro[4.4]nonan-1-one, containing a protected ketone functionality. Protection of the amine (by, for instance, reaction with ethyl chlorformate), deprotection of the ketone, coupling with the appropriate Grignard or organolithium reagent, dehydration of the resulting hydroxy group, and deprotection of the amine will provide the desired azaspiroalkene compounds. Reduction of the double bond will provide the desired azaspiroalkane compounds.

Alternatively, the ethyl cyclopentanecarboxylate, containing the protected ketone functionality, can be deprotonated with LDA and allowed to react with an alkylating agent such as bromo or chloroacetonitrile, then subjected to nitrile reduction and cyclization as reported by Culbertson et al., J. Med. Chem. 33:2270 (1990). Alternatively, following deprotonation, the deprotonated intermediate can be allowed to react with an alkylating agent such as allyl bromide. The resulting olefin can then be oxidatively cleaved to an aldehyde, as reported by Genin et al., J. Org. Chem. 58:2334 (1993); Hinds et al., J. Med. Chem. 34:1777 (1991); Kim et al., J. Org. Chem. 61:3138 (1996); EP 0 360 390 and U.S. Pat. No. 5,733,912. The aldehyde can then be subjected to reductive amination with an ammonium salt or primary aliphatic or aromatic amine, according to methods known to those skilled in the art. Alternatively, the aldehyde can be reduced to the corresponding alcohol and the alcohol then transformed to an amine by conversion to a leaving group, followed by displacement with the appropriate amine. This can also be achieved by displacing the leaving group with an azide ion and subsequently reduction to the primary amine using methods known to those skilled in the art. The alcohol can also be converted to an amine using Mitsunobu conditions. The resulting intermediate can be cyclized to a spirolactam by methods known to those skilled in the art, such as heating in a suitable solvent with or without an acidic or basic catalyst. Reduction of the lactam to the amine, protection of the amine, deprotection of the ketal, coupling with the appropriate Grignard or organolithium reagent, and dehydration of the resulting alcohol, will provide the desired azaspiroalkene compounds. Reduction of the double bond will provide the desired azaspiroalkane compounds.

The compounds of Formula 1, which include a 2-azaspiro[4.5]decane core, can be prepared according to a modification of various teachings (*Helv. Chim. Acta* 60:1650 (1977); Smith et al., *J. Med. Chem.* 38(19):3772 (1995); Elliott et al., *Biorg. Med. Chem. Lett.* 8:1851 (1998)). Thus, a mono-protected 1,4-cyclohexanedione can be converted to the protected 4-oxocyclohexylideneacetic acid ester via Wittig olefination. Subsequent Michael addition with the anion of nitromethane, followed by reduction of the nitro group with Raney nickel and spontaneous cyclization, provides the protected 2-azaspiro[4.5]decane-3,8-dione. Treatment of this with a reducing agent, such as lithium aluminum hydride, protection of the resulting amine, and removal of the protecting group from the ketone, provides the 2-azaspiro[4.5]decan-8-one with a carbonyl ready to couple with the appropriate aryl or heteroaryl Grignard or organolithium reagent. Following the coupling reaction, the resulting alcohol can be dehydrated to form the desired azaspiroalkene compounds. The double bond can be hydrogenated to form the desired azaspiroalkane compounds.

Additional Ring Systems

Chemistry such as that described above can be applied to alkyl oxocycloalkanecarboxylates of varying ring sizes. The deprotonation alpha to the ester group in the ring is not dependent on the ring size. The subsequent steps described above, resulting in cyclization to form the spiro-fused ring, similarly do not depend on the size of the ring that includes the ester group (rather, these steps are based on intramolecular cyclization to form the spiro-fused ring). The deprotection of the oxo group, and subsequent coupling step, similarly does not depend on the size of the ring. As the driving force for formation of the double bond alpha to the aryl/heteroaryl ring is the conjugation of the resulting double bond with the aryl/heteroaryl ring, the size of the ring containing the oxo group similarly does not significantly affect the chemistry. Finally, the hydrogenation of the resulting double bond is unaffected by the ring size. Accordingly, using the chemistry outlined above with respect to the cyclopentane rings, one of skill in the art can readily apply this teaching to form the other exemplified ring systems.

High Throughput Synthesis

The coupling reactions described in this application are amenable to high through-put synthetic techniques. Thus a library of compounds of the present invention can be produced by coupling, in a 96-well plate format, for instance, various haloarenes with various azaspiro compounds.

Preparation of Single Enantiomer Compounds

Single enantiomer compounds can be prepared using various methods. One method, well known to those skilled in the art of organic synthesis, involves resolution using diastereomeric salts. Compounds of the present invention contain basic nitrogen atoms and will react with acids to form crystalline salts. Various acids, carboxylic and sulfonic, are commercially available in enantiomerically pure form. Examples include tartaric, dibenzoyl- and di-p-toluoyltartaric, and camphorsulfonic acids. When any one of these or other single enantiomer acids is reacted with a racemic amine base, diastereomeric salts result. Fractional crystallization of the salts, and subsequent regeneration of the bases, results in enantiomeric resolution thereof.

Selective synthesis of single enantiomers can also be accomplished by methods known to those skilled in the art. Such methods will vary as the chemistry used for construction of the azaspiro rings varies.

Separation of Double Bond Regioisomers

Also, in some cases, the dehydration step will provide a mixture of double bond-containing compounds, where the dehydration occurs between the carbon including the hydroxy group and either of the two adjacent carbons (where deprotonation occurs). These regioisomeric compounds can be separated using chromatography or other known means, or, if desired, the double bonds can be hydrogenated to yield the same azaspiroalkane compound.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more compounds of Formula 1, prodrugs or metabolites thereof, and/or pharmaceutically acceptable salts thereof. Optically active compounds can be employed as racemic mixtures or as pure enantiomers.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via infusion or injection (e.g., as a suspension or as an emulsion in a pharmaceutically acceptable liquid or mixture of liquids). Compositions can be injected intraveneously, intramuscularly, subcutaneously, intraperitoneally, intraarterially, intrathecally; and intracerebroventricularly. Suitable carriers for injection are well known to those of skill in the art, and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect the functioning of the CNS. More specifically, in treating a CNS disorder, preferable administration is designed to optimize the effect upon those relevant receptor subtypes that have an effect upon the functioning of the CNS, while minimizing the effects upon muscle-type receptor subtypes. Other suitable methods for administering the compounds of the present invention are described in U.S. Pat. No. 5,604,231 to Smith et al.

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anaesthetics, steroids, vitamins, minerals and corticosteroids. Such components can provide additional therapeutic benefit, act to affect the therapeutic action of the pharmaceutical composition, or act towards preventing any potential side effects, which can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds, when employed in effective amounts in accordance with the method described herein, are selective to certain relevant nicotinic receptors, but do not significantly activate receptors associated with undesirable side effects at concentrations at least greater than those required for modulating the function of relevant receptors and/or the release of neurotransmitters. By this is meant that a particular dose of compound effective in preventing and/or treating a CNS disorder is essentially ineffective in eliciting activation of certain ganglionic-type nicotinic receptors at concentration higher than 5 times, preferably higher than 100 times, and more preferably higher than 1,000 times than those required for modulation of neurotransmitter release, for instance. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for modulation of CNS recector function.

The compounds described herein, when employed in effective amounts in accordance with the methods described herein, can provide some degree of prevention of the progression of CNS disorders, ameliorate symptoms of CNS disorders, and ameliorate to some degree of the recurrence of CNS disorders. The effective amounts of those compounds are typically below the threshold concentration required to elicit any appreciable side effects, for example those effects relating to skeletal muscle. The compounds can be administered in a therapeutic window in which certain CNS disorders are treated and certain side effects are avoided. Ideally, the effective dose of the compounds described herein is sufficient to provide the desired effects upon the CNS but is insufficient (i.e., is not at a high enough level) to provide undesirable side effects. Preferably, the compounds are administered at a dosage effective for treating the CNS disorders but less than $\frac{1}{5}$, and often less than $\frac{1}{10}$, the amount required to elicit certain side effects to any significant degree.

Most preferably, effective doses are at very low concentrations, where maximal effects are observed to occur, with a minimum of side effects. administering the compound in an amount of less than 5 mg/kg of patient weight. Often, the compounds of the present invention are administered in an amount from less than about 1 mg/kg patent weight and usually less than about 100 µg/kg of patient weight, but frequently between about 10 µg to less than 100 µg/kg of patient weight. For compounds that do not induce effects on muscle-type nicotinic receptors at low concentrations, the effective dose is less than 5 mg/kg of patient weight; and often such compounds are administered in an amount from 50 µg to less than 5 mg/kg of patient weight. The foregoing effective doses typically represent that amount administered as a single dose, or as one or more doses administered over a 24-hour period. In addition, administration of the effective dose is such that the concentration of the compound within the plasma of the patient normally does not exceed 500 ng/mL and frequently does not exceed 100 ng/mL.

In one embodiment, upon administration, the active ingredients interact with receptor sites, within the body of the subject, that control dopamine release. The ability of these compounds to modulate the release of dopamine is especially significant, as it indicates that the compounds can be useful in interrupting the dopamine reward system (when the modulation is inhibition), and thus in treating disorders that are mediated by it. Such disorders include substance abuse, tobacco use and weight gain that accompanies drug cessation.

In this embodiment, the compounds described herein are a useful alternative in treating dependencies on drugs of abuse including alcohol, amphetamines, barbiturates, benzodiazepines, caffeine, cannabinoids, cocaine, hallucinogens, opiates, phencyclidine and tobacco and the treatment of eating disorders such as obesity that occurs following drug cessation while reducing side effects associated with the use of psychomotor stimulants (agitation, sleeplessness, addiction, etc.).

The compounds also advantageously affect the functioning of the CNS, in a manner which is designed to optimize the effect upon those relevant receptor subtypes that have an effect upon dopamine release, while minimizing the effects upon muscle-type receptor subtypes.

Preferably, the compositions are administered such that active ingredients interact with regions where dopamine production is affected or occurs. In some embodiments, the compounds are very potent at affecting doamine production and/or secretion at very low concentrations, and are very efficacious (i.e., they modulate dopamine production and/or secretion to an effective degree).

In certain circumstances, the compounds described herein can be employed as part of a pharmaceutical composition with other compounds intended to prevent or treat drug addiction, nicotine addiction, and/or obesity. In addition to effective amounts of the compounds described herein, the pharmaceutical compositions can also include various other components as additives or adjuncts. Exemplary pharmaceutically acceptable components or adjuncts which are employed in relevant circumstances include antidepressants, antioxidants, free-radical scavenging agents, peptides, growth factors, antibiotics, bacteriostatic agents, immunosuppressives, anticoagulants, buffering agents, anti-inflammatory agents, anti-pyretics, time-release binders, anaesthetics, steroids, vitamins, minerals and corticosteroids. Such components can provide additional therapeutic benefit, act to affect the therapeutic action of the pharmaceutical composition, or act towards preventing any potential side effects which can be imposed as a result of administration of the pharmaceutical composition.

IV. Methods of Using the Compounds and/or Pharmaceutical Compositions

The compounds can be used to treat those types of conditions and disorders for which other types of nicotinic compounds have been proposed as therapeutics. See, for example, Williams et al., *Drug News Perspec.* 7(4):205 (1994), Arneric et al., *CNS Drug Rev.* 1(1):1 (1995), Arneric et al., *Exp. Opin. Invest Drugs* 5(1):79 (1996), Bencherif et al., *J. Pharmacol. Exp. Ther.* 279:1413 (1996), Lippiello et al., *J. Pharmacol. Exp. Ther.* 279:1422 (1996), Damaj et al., *J. Pharmacol. Exp. Ther.* 291:390 (1999); Chiari et al., *Anesthesiology* 91:1447 (1999); Lavand'homme and Eisenbach, *Anesthesiology* 91:1455 (1999); *Neuroscience* (1997), Holladay et al., *J. Med. ChemChem.* 40(28):4169 (1997), Bannon et al., *Science* 279:77 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al., the disclosures of which are incorporated herein by reference in their entirety.

The compounds can also be used as adjunct therapy in combination with existing therapies in the management of the aforementioned types of diseases and disorders. In such situations, it is preferably to administer the active ingredients to in a manner that optimizes effects upon abnormal cytokine production, while minimizing effects upon receptor subtypes such as those that are associated with muscle and ganglia. This can be accomplished by targeted drug delivery and/or by adjusting the dosage such that a desired effect is obtained without meeting the threshold dosage required to achieve significant side effects.

Treatment of CNS Disorders

The compounds described herein are effective at treating a wide variety of CNS disorders. Examples of CNS disorders that can be treated in accordance with the present invention include pre-senile dementia (early onset Alzheimer's disease), senile dementia (dementia of the Alzheimer's type), Lewy Body dementia, HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome.

CNS disorders can be treated and/or prevented by administering to a patient an amount of a compound or pharmaceutical composition effective for providing some degree of prevention of the progression of a CNS disorder (i.e., provide protective effects), amelioration of the symptoms of a CNS disorder, and amelioration of the recurrence of a CNS disorder. The method involves administering an effective amount of a compound selected from the general formulae, which are set forth hereinbefore.

Other Disorders

In addition to treating CNS disorders, the pharmaceutical compositions can be used to prevent or treat certain other conditions, diseases and disorders. Examples include neurodegenerative diseases, autoimmune disorders such as Lupus, disorders associated with cytokine release, anti-inflammatory uses, as well as those indications set forth in PCT WO 98/25619. The pharmaceutical compositions can ameliorate many of the symptoms associated with those conditions, diseases and disorders.

Modulation (such as inhibition) of cytokine release is desirable in the treatment of cachexia, inflammation, neurodegenerative diseases, viral infection, and neoplasia. The cachexia is often secondary to infection (e.g., as occurs in AIDS, AIDS-related complex and neoplasia) or to cancer therapy. Examples of inflammatory disorders that can be treated include acute cholangitis, aphthous stomatitis, asthma, ulcerative colitis, inflammatory bowel disease, pouchitis, viral pneumonitis and arthritis (e.g., rheumatoid arthritis and osteoarthritis).

The pharmaceutical compositions can also be used as anti-infectious agents (e.g, for treating bacterial, fungal and viral infections, as well as the effects, such as sepsis, of other types of toxins).

The compounds can be used as analgesics, to treat convulsions such as those that are symptomatic of epilepsy, to treat conditions such as syphillis and Creutzfeld-Jakob disease.

The compounds can also be appropriately synthesized and used as or within pharmaceutical compositions that are used as diagnostic probes.

The compounds useful according to the method of the present invention have the ability to bind to and modulate the function of nicotinic cholinergic receptors of the brain of the patient (e.g., such as those receptors that modulate dopamine release). The receptor binding constants of typical compounds useful in carrying out the present invention generally exceed about 0.1 nM, often exceed about 1 nM, and frequently exceed about 10 nM. The receptor binding constants of such typical compounds generally are less than about 1 μM often are less than about 100 nM, and frequently are less than about 50 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds of the present invention, when employed in effective amounts in accordance with the method of the present invention, lack the ability to elicit activation of nicotinic receptors of human muscle to any significant degree. In that regard, the compounds of the-present invention demonstrate poor ability to cause isotopic rubidium ion flux through nicotinic receptors in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 μM). Generally, typical preferred compounds useful in carrying the present invention activate isotopic rubidium ion flux by less than 10 percent, often by less than 5 percent, of that maximally provided by S(−) nicotine.

The compounds, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical preferred compounds useful in carrying out the present invention activate isotopic rubidium ion flux by less than 10 percent, often by less than 5 percent, of that maximally provided by S(−) nicotine.

The compounds, when employed in effective amounts in accordance with the method of the present invention, are effective towards providing some degree of prevention of the progression of CNS disorders, amelioration of the symptoms of CNS disorders, and amelioration to some degree of the recurrence of CNS disorders. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less ⅓, frequently less than ⅕, and often less than ¹⁄₁₀, that amount sufficient to cause any side effects to a significant degree.

Treatment of Addiction

The compounds can be used to treat drug addiction, nicotine addiction and/or obesity, such as the obesity associated with drug cessation. The compounds can also be used as adjunct therapy in combination with existing therapies in the management of the aforementioned types of diseases and disorders. In such situations, it is preferable to administer the active ingredients to in a manner that optimizes effects upon dopamine production and/or secretion, while minimizing effects upon receptor subtypes such as those that are associated with muscle and ganglia. This can be accomplished by targeted drug delivery and/or by adjusting the dosage such that a desired effect is obtained without meeting the threshold dosage required to achieve significant side effects.

The compounds, when employed in effective amounts as described herein, are selective to certain relevant nicotinic receptors, but do not significantly activate receptors associated with undesirable side effects. By this is meant that a particular dose of compound that is effective at suppressing dopamine production and/or release is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue.

Those compounds effective at suppressing of dopamine production and/or release can be used to treat drug addiction, nicotine addiction, and/or obesity at effective at concentrations that are not sufficient to elicit any appreciable side effects, as is demonstrated by decreased effects on preparations believed to reflect effects on the cardiovascular system, or effects to skeletal muscle. As such, administration of the compounds provides a therapeutic window in which treatment of drug addiction, nicotine addiction and/or obesity is effected, and side effects are avoided. That is, an effective dose of a compound of the present invention is sufficient to provide the desired effects on dopamine production and/or secretion, but is insufficient (i.e., is not at a high enough level) to provide undesirable side effects. Preferably, the compounds results in treatment of drug addiction, nicotine addiction and/or obesity upon administration of less ⅓, frequently less than ⅕, and often less than ¹⁄₁₀ that amount sufficient to cause any side effects to a significant degree.

V. Biological Assays

Radioligand Binding at CNS nAChR
α4β2 Subtype

Rats (female, Sprague-Dawley), weighing 150-250 g, are maintained on a 12 h light/dark cycle and are allowed free access to water and food supplied by PMI Nutrition International, Inc. Animals are anesthetized with 70% $CO_2$, then decapitated. Brains are removed and placed on an ice-cold platform. The cerebral cortex was removed and placed in 20 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 4 mg protein/ml Protein was determined by the method of Lowry et al., *J. Biol. Chem.* 193: 265 (1951), using bovine serum albumin as the standard.

The binding of [$^3$H]nicotine was measured using a modification of the methods of Romano et al., *Science* 210: 647 (1980) and Marks et al., *Mol. Pharmacol.* 30: 427 (1986). The [$^3$H]nicotine (Specific Activity=81.5 Ci/mmol) was obtained from NEN Research Products. The binding of [$^3$H]nicotine was measured using a 3 h incubation at 4° C. Incubations are conducted in 48-well micro-titre plates and contained about 400 µg of protein per well in a final incubation volume of 300 µL. The incubation buffer was PBS and the final concentration of [$^3$H]nicotine was 5 nM. The binding reaction was terminated by filtration of the protein containing bound ligand onto glass fiber filters (GF/B, Brandel) using a Brandel Tissue Harvester at 4° C. Filters are soaked in de-ionized water containing 0.33% polyethyleneimine to reduce non-specific binding. Each filter was washed with ice-cold buffer (3×1 ml). Non-specific binding was determined by inclusion of 10 µM non-radioactive L-nicotine (Acros Organics) in selected wells.

The inhibition of [$^3$H]nicotine binding by test compounds was determined by including seven different concentrations of the test compound in selected wells. Each concentration was replicated in triplicate. $IC_{50}$ values are estimated as the concentration of compound that inhibited 50 percent of specific [$^3$H]nicotine binding. Inhibition constants (Ki values), reported in nM, are calculated from the $IC_{50}$ values using the method of Cheng et al., *Biochem. Pharmacol.* 22: 3099 (1973).

α7 Subtype

Rats (female, Sprague-Dawley), weighing 150-250 g, are maintained on a 12 h light/dark cycle and are allowed free access to water and food supplied by PMI Nutrition International, Inc. Animals are anesthetized with 70% $CO_2$, then decapitated. Brains are removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 µM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/ml. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999). [$^3$H]MLA (Specific Activity=25-35 Ci/mmol) was obtained from Tocris. The binding of [$^3$H]MLA was determined using a 2 h incubation at 21° C. Incubations are conducted in 48-well micro-titre plates and contained about 200 µg of protein per well in a final incubation volume of 300 µL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters are soaked in de-ionized water containing 0.33% polyethyleneimine to reduce non-specific binding. Each filter was washed with PBS (3×1 ml) at room temperature. Non-specific binding was determined by inclusion of 50 µM non-radioactive MLA in selected wells.

The inhibition of [$^3$H]MLA binding by test compounds was determined by including seven different concentrations of the test compound in selected wells. Each concentration was replicated in triplicate. $IC_{50}$ values are estimated as the concentration of compound that inhibited 50 percent of specific [$^3$H]MLA binding. Inhibition constants (Ki values), reported in nM, are calculated from the $IC_{50}$ values using the method of Cheng et al., *Biochem. Pharmacol.* 22: 3099-3108 (1973).

Determination of Dopamine Release

Dopamine release is measured using striatal synaptosomes obtained from rat brain, according to the procedures set forth by Rapier et al., *J. Neurochem.* 54: 937 (1990). Rats (female, Sprague-Dawley), weighing 150-250 g, are maintained on a 12 h light/dark cycle and are allowed free access to water and food supplied by PMI Nutrition International, Inc. Animals are anesthetized with 70% $CO_2$, then decapitated. The brains are quickly removed and the striata dissected. Striatal tissue from each of 2 rats is pooled and homogenized in ice-cold 0.32 M sucrose (5 ml) containing 5 mM HEPES, pH 7.4, using a glass/glass homogenizer. The tissue is then centrifuged at 1,000×g for 10 min. The pellet is discarded and the supernatant is centrifuged at 12,000×g for 20 min. The resulting pellet is re-suspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 min at 25,000×g. The final pellet is resuspended in perfusion buffer (1.4 ml) for immediate use.

The synaptosomal suspension is incubated for 10 min at 37° C. to restore metabolic activity. [3H]Dopamine ([$^3$H] DA, specific activity=28.0 Ci/mmol, NEN Research Products) is added at a final concentration of 0.1 µM and the suspension is incubated at 37° C. for another 10 min. Aliquots of tissue (50 µl) and perfusion buffer (100 µl) are loaded into the suprafusion chambers of a Brandel Suprafusion System (series 2500, Gaithersburg, Md.). Perfusion buffer (room temperature) is pumped into the chambers at a rate of 3 ml/min for a wash period of 8 min. Test compound (10 µM) or nicotine (10 µM) is then applied in the perfusion stream for 40 sec. Fractions (12 sec each) are continuously collected from each chamber throughout the experiment to capture basal release and agonist-induced peak release and to re-establish the baseline after the agonist application. The perfusate is collected directly into scintillation vials, to which scintillation fluid is added. [$^3$H]DA released is quantified by scintillation counting. For each chamber, the integrated area of the peak is normalized to its baseline.

Release is expressed as a percentage of release obtained with an equal concentration of L-nicotine. Within each assay, each test compound is replicated using 2-3 chambers; and replicates are averaged. When appropriate, dose-response curves of test compound are determined. The maximal activation for individual compounds (Emax) is determined as a percentage of the maximal activation induced by L-nicotine. The compound concentration resulting in half maximal activation ($EC_{50}$) of specific ion flux is also defined.

Selectivity vs. Peripheral nAChRs

Interaction at the Human Muscle Subtype

Activation of muscle-type nAChR can be established on the human clonal line TE671/RD, which is derived from an embryonal rhabdomyosarcoma (Stratton et al., *Carcinogen* 10: 899 (1989)). These cells express receptors that have pharmacological (Lukas, *J. Pharmacol. Exp. Ther.* 251: 175 (1989)), electrophysiological (Oswald et al., *Neurosci. Lett.* 96: 207 (1989)), and molecular biological profiles (Luther et al., *J. Neurosci.* 9: 1082 (1989)) similar to the muscle-type nAChR.

TE671/RD cells can be maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells can be cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells are 80% confluent, they are plated to 6 well polystyrene plates (Costar). Experiments are typically conducted when the cells reached 100% confluency.

Nicotinic acetylcholine receptor (nAChR) function can be assayed using $^{86}Rb^+$ efflux according to the method described by Lukas et al., *Anal. Biochem.* 175: 212 (1988). On the day of the experiment, growth media is gently removed from the well and growth media containing Rubidium chloride ($10^6$ µCi/ml) is added to each well. Cells are incubated at 37° C. for a minimum of 3 h. After the loading period, excess $^{86}Rb^+$ is removed and the cells are washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells are exposed to either 100 µM of test compound, 100 µM of L-nicotine (Acros Organics) or buffer alone for 4 min. Following the exposure period, the supernatant containing the released $^{86}Rb^+$ is removed and transferred to scintillation vials. Scintillation fluid is added and released radioactivity is measured by liquid scintillation counting.

Within each assay, each point had 2 replicates, which are averaged. The amount of $^{86}Rb^+$ release is compared to both a positive control (100 µM L-nicotine) and a negative control (buffer alone) to determine the percent release relative to that of L-nicotine.

When appropriate, dose-response curves of test compound are determined. The maximal activation for individual compounds (Emax) is determined as a percentage of the maximal activation induced by L-nicotine. The compound concentration resulting in half maximal activation ($EC_{50}$) of specific ion flux is also determined.

Interaction at the Rat Ganglionic Subtype

Activation of rat ganglion nAChR is established on the pheochromocytoma clonal line PC12, which is a continuous clonal cell line of neural crest origin, derived from a tumor of the rat adrenal medulla. These cells express ganglion-like neuronal nicotinic receptors (see Whiting et al., *Nature* 327: 515 (1987); Lukas, *J. Pharmacol. Exp. Ther.* 251: 175 (1989); Whiting et al., *Mol. Brain Res.* 10: 61 (1990)).

Rat PC12 cells are maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells are cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells are 80% confluent, they are plated to 6 well Nunc plates (Nunclon) and coated with 0.03% poly-L-lysine (Sigma, dissolved in 100 mM boric acid). Experiments are conducted when the cells reached 80% confluency.

Nicotinic acetylcholine receptor (nAChR) function is assayed using $^{86}Rb^+$ efflux according to a method described by Lukas et al., *Anal. Biochem.* 175: 212 (1988). On the day of the experiment, growth media is gently removed from the well and growth media containing $^{86}$Rubidium chloride ($10^6$ µCi/ml) is added to each well. Cells are incubated at 37° C. for a minimum of 3 h. After the loading period, excess $^{86}Rb^+$ is removed and the cells are washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells are exposed to either 100 µM of test compound, 100 µM of nicotine or buffer alone for 4 min. Following the exposure period, the supernatant containing the released $^{86}Rb^+$ is removed and transferred to scintillation vials. Scintillation fluid is added and released radioactivity is measured by liquid scintillation counting.

Within each assay, each point had 2 replicates, which are averaged. The amount of $86Rb^+$ release is compared to both a positive control (100 µM nicotine) and a negative control (buffer alone) to determine the percent release relative to that of L-nicotine.

When appropriate, dose-response curves of test compound are determined. The maximal activation for individual compounds (Emax) is determined as a percentage of the maximal activation induced by L-nicotine. The compound concentration resulting in half maximal activation ($EC_{50}$) of specific ion flux is also determined.

Interaction at the Human Ganglionic Subtype

The cell line SH-SY5Y is a continuous line derived by sequential subcloning of the parental cell line, SK-N-SH, which is originally obtained from a human peripheral neuroblastoma. SH-SY5Y cells express a ganglion-like nAChR (Lukas et al., *Mol. Cell. Neurosci.* 4: 1 (1993)).

Human SH-SY5Y cells are maintained in proliferative growth phase according to routine protocols (Bencherif et al., *Mol. Cell. Neurosci.* 2: 52 (1991) and Bencherif et al., J. Pharmacol. Exp. Ther. 257: 946 (1991)). Cells are cultured in Dulbecco's modified Eagles medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells are 80% confluent, they are plated to 6 well polystyrene plates (Costar). Experiments are conducted when the cells reached 100% confluency.

Nicotinic acetylcholine receptor (nAChR) function is assayed using $^{86}Rb^+$ efflux according to a method described by Lukas et al., *Anal. Biochem.* 175: 212 (1988). On the day of the experiment, growth media is gently removed from the well and growth media containing $^{86}$Rubidium chloride ($10^6$ µCi/ml) is added to each well. Cells are incubated at 37° C. for a minimum of 3 h. After the loading period, excess $^{86}Rb^+$ is removed and the cells are washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4), taking care not to disturb the cells. Next, cells are exposed to either 100 µM of test compound, 100 µM of nicotine, or buffer alone for 4 min. Following the exposure period, the supernatant containing the released $^{86}Rb^+$ is removed and transferred to scintillation vials. Scintillation fluid is added and released radioactivity is measured by liquid scintillation counting.

Within each assay, each point had 2 replicates, which are averaged. The amount of $^{86}Rb^+$ release is compared to both a positive control (100 µM nicotine) and a negative control (buffer alone) to determine the percent release relative to that of L-nicotine.

When appropriate, dose-response curves of test compound are determined. The maximal activation for individual compounds (Emax) is determined as a percentage of the maximal activation induced by L-nicotine. The compound concentration resulting in half maximal activation ($EC_{50}$) of specific ion flux is also defined.

Selectivity

The selectivity of the compounds for a given receptor can be evaluated by comparing the binding of the compounds to different receptors using known methodology.

SYNTHETIC EXAMPLES

The following synthetic examples are provided to illustrate the present invention and should not be construed as limiting the scope thereof. In these examples, all parts and percentages are by weight, unless otherwise noted. Reaction yields are reported in mole percentages. Column chromatography is done using Merck silica gel 60 (70-230 mesh). Pressure reactions were done in a heavy wall glass pressure tube (185 mL capacity), with Ace-Thread, and plunger valve available from Ace Glass Inc. Reaction mixtures were typically heated using a high-temperature silicon oil bath, and temperatures refer to those of the oil bath. The following abbreviations are used in the following examples: $CHCl_3$ for chloroform, $CH_2Cl_2$ for dichloromethane, $CH_3OH$ for methanol, DMF for N,N-dimethylformamide, and EtOAc for ethyl acetate, THF for tetrahydrofuran, and $Et_3N$ for triethylamine. In these examples, all parts and percentages are by weight, unless otherwise noted. Reaction yields are reported in mole percentage.

Example 1

Synthesis of 1-aza-8-(3-pyridinyl)spiro[4.5]dec-7-ene trifluoroacetate 1-aza-8-(3-pyridinyl)spiro[4.5]dec-7-ene trifluoroacetate was prepared in accordance with the following techniques:

1-Azaspiro[4.5]decan-2,8-dione ethylene ketal was made as described in *Org. Lett.* 3(15): 2353-2356 (2001).

1-Azaspiro[4.5]decan-8-one ethylene ketal

A solution of 1-azaspiro[4.5]decan-2,8-dione ethylene ketal (5.00 g, 23.7 mmol) in dry THF (100 mL) was added to lithium aluminum hydride (0.90 g, 23.7 mmol) under argon. The mixture was refluxed for 8 h and cooled to 0° C., whereupon aqueous sodium hydroxide (5 M), sufficient to decompose the remaining hydride and produce a granular precipitate of aluminum salts, was added. The mixture was filtered, and the filtrate was concentrated by rotary evaporation, leaving 4.50 g (96%) of a viscous, colorless oil.

Ethyl 1-azaspiro[4.5]decan-8-one-1-carboxylate

Ethyl chloroformate (1.90 mL, 2.16 g, 19.9 mmol) was added drop-wise to a cold (0° C.), stirred solution of 1-azaspiro[4.5]decan-8-one ethylene ketal (3.00 g, 15.2 mmol), triethylamine (3.20 mL, 2.32 g, 23.0 mmol) and catalytic 4-(dimethylamino)pyridine (10 mg) in dry dichloromethane (25 mL) under a nitrogen atmosphere. The ice bath was removed and the reaction was stirred 4 h at ambient temperature and poured into saturated aqueous sodium bicarbonate (10 mL). The mixture was shaken and the organic layer drawn off. The aqueous layer was extracted with dichloromethane (25 mL), and the combined dichloromethane extracts were dried ($Na_2SO_4$) and concentrated by rotary evaporation. The residue (3.5 g) was combined with 2% aqueous sulfuric acid (50 mL) and stirred 3 h at ambient temperature. The mixture was extracted with ethyl acetate (4×20 mL), and the combined extracts were washed successively with saturated aqueous sodium bicarbonate and saturated aqueous sodium chloride (10 mL each) and dried ($Na_2SO_4$). The residue from concentration of the dried extracts was dissolved dichloromethane (100 mL) and stirred for 1 h with silica gel (5 g). The silica gel was then removed by filtration, and the filtrate was concentrated, leaving 2.35 g (68.7%) of viscous colorless oil.

Ethyl 1-aza-8-(3-pyridinyl)spiro[4.5]dec-7-ene-1-carboxylate n-Butyllithium (2.30 mL of 2.5 M in hexane, 5.8 mmol) was added drop-wise to a solution of 3-bromopyridine (0.91 g, 5.77 mmol) in dry THF (5 mL) at −78° C. under nitrogen. This mixture was stirred for 30 min at −78° C. and cannulated into a solution of ethyl 1-azaspiro[4.5]decan-8-one-1-carboxylate (1.00 g, 4.44 mmol) in dry THF (20 mL), also at −78° C. under nitrogen. The mixture was allowed to warm to ambient temperature as it stirred overnight. It was then quenched with saturated aqueous ammonium chloride (5 mL) and extracted with dichloromethane (3×10 mL). The extracts were dried ($Na_2SO_4$) and concentrated by rotary evaporation, and the residue was column chromatographed on silica gel, using 95:5 chloroform/methanol as the eluent. Concentration of selected fractions gave a viscous light brown oil which was dissolved in 98% formic acid (3 mL) and heated at 100° C. under nitrogen for 12 h. The formic acid was removed by repeated azeoptropic evaporation with toluene, and the residue as treated with saturated aqueous sodium bicarbonate (2 mL) and extracted with dichloromethane (3×5 mL). The extracts were dried ($Na_2SO_4$) and concentrated by rotary evaporation. The residue was column chromatographed on silica gel, using 97:3 chloroform/methanol as eluent. Concentration of selected fractions gave 0.50 g of nearly colorless, viscous oil (~40%).

1-Aza-8-(3-pyridinyl)spiro[4.5]dec-7-ene trifluoroacetate

Ethyl 1-aza-8-(3-pyridinyl)spiro[4.5]dec-7-ene-1-carboxylate (0.300 g, 1.05 mmol) was combined with 12 M HCl (5 mL), and the mixture was refluxed overnight under nitrogen. The volatiles were removed under vacuum, and the residue was combined with saturated aqueous sodium bicarbonate (5 mL) and extracted with chloroform (3×25 mL). The combined extracts were dried ($Na_2SO_4$) and concentrated. The resulting viscous brown liquid was purified by high-pressure liquid chromatography on C18 silica, using a gradient of acetonitrile in water (0.1% trifluoroacetic acid), to give 120 mg (35%) of viscous, colorless oil.

Example 2

Synthesis of 1-aza-8-(5-isopropoxy-3-pyridinyl)spiro[4.5]dec-7-ene trifluoroacetate 1-Aza-8-(5-isopropoxy-3-pyridinyl)spiro[4.5]dec-7-ene trifluoroacetate was prepared in accordance with the following techniques:

5-Isopropoxy-3-pyridinylboronic acid

To a stirred, −78° C. solution of 2.5 M n-butyllithium (44.0 mL, 110 mmol) in toluene (120 mL) was slowly added a solution of 3-bromo-5-isopropoxypyridine (21.6 g, 100 mmol) in toluene (40 mL) while maintaining the temperature below −50° C. After the addition was complete, the reaction was stirred at −78° C. for 30 min. Distilled THF (40 mL) was added, and the reaction stirred for 15 min at −78° C., followed by the addition of triisopropylborate (27.7 mL, 120 mmol) in one portion. After warming to −15° C., the reaction was quenched with 1M HCl (260 mL), and stirred for one hour. The mixture was then neutralized (to pH 7) with 5 M NaOH and extracted with THF (4×100 mL). The combined extracts were dried ($Na_2SO_4$), filtered and concentrated. The residue was dissolved in 1:1 THF/MeOH, filtered, concentrated, and dissolved in warm acetonitrile. Upon cooling, the acetonitrile solution deposited a light brown powder, which was collected by filtration and vacuum dried (8.94 g, 49%).

Ethyl 1-aza-8-((trifluoromethyl)sulfonyloxy)spiro[4.5]dec-7-ene-1-carboxylate A solution of lithium diisopropylamide was produced by adding n-butyllithium (2.13 mL of 2.5 M in hexane, 5.33 mmol) to a mixture of diisopropylamine (0.74 mL, 0.54 g, 5.3 mmol) in dry THF (5 mL) at −78° C. under nitrogen. After stirring for 20 min, the lithium diisopropylamide solution was treated drop-wise with a solution of ethyl 1-azaspiro[4.5]decan-8-one-1-carboxylate (1.00 g, 4.44 mmol) in dry THF (5 mL). The mixture was warmed briefly to −40° C., and returned to −78° C., whereupon 2-(N,N-bis(trifluormethylsulfonyl)amino)-5-chloropyridine (3.49 g, 8.89 mmol) was added in one portion. The mixture was warmed slowly to ambient temperature (3 h period), treated with saturated aqueous sodium bicarbonate (10 mL) and extracted with ethyl acetate (3×15 mL). The combined extracts were washed successively with 1 M HCl (5 mL), saturated aqueous sodium bicarbonate (15 mL) and saturated aqueous sodium chloride (15 mL), dried ($Na_2SO_4$) and concentrated by rotary evaporation. The residue was column chromatographed on silica gel, using 3:7 ethyl acetate/hexane as eluent. Concentration of selected fractions gave 1.10 g (76%) of viscous oil.

Ethyl 1-aza-8-(5-isopropoxy-3-pyridinyl)spiro[4.5]dec-7-ene-1-carboxylate

Ethyl 1-aza-8-((trifluoromethyl)sulfonyloxy)spiro[4.5]dec-7-ene-1-carboxylate (1.00 g, 2.80 mmol), 5-isopropoxy-3-pyridinylboronic acid (1.01 g, 5.60 mmol), lithium chloride (0.35 g, 8.2 mmol), saturated aqueous sodium carbonate (10 mL) and dimethoxyethane (30 mL) were combined in a flask. The flask was alternatively evacuated and filled with argon three times. Tetrakis(triphenylphosphine)palladium (0) (325 mg, 0.28 mmol) was then added, and the mixture was heated at 100° C. for 3 h. The reaction mixture was cooled, diluted with water (10 mL) and extracted with dichloromethane (4×15 mL). The combined extracts were dried ($Na_2SO_4$) and concentrated by rotary evaporation. Column chromatographic purification on silica gel, using 7:3 ethyl acetate/hexane as eluent, yielded 750 mg (81.6%) of viscous oil.

1-Aza-8-(5-isopropoxy-3-pyridinyl)spiro[4.5]dec-7-ene trifluoroacetate

Ethyl 1-aza-8-(5-isopropoxy-3-pyridinyl)spiro[4.5]dec-7-ene-1-carboxylate (200 mg, 0.610 mmol), potassium hydroxide (102 mg, 1.82 mmol), hydrazine hydrate (1 mL) were dissolved in ethylene glycol (5 mL) and heated at 100° C. overnight. The mixture was cooled, diluted with water (5 mL) and extracted with chloroform (5×10 mL). The combined extracts were dried ($Na_2SO_4$) and concentrated by rotary evaporation. High-pressure liquid chromatographic purification of the residue on C18 silica gel, using a gradient of acetonitrile in water (0.1% trifluoroacetic acid), gave 108 mg (46%) of viscous, light brown oil.

Example 3

Synthesis of N-methyl-1-aza-8-(5-isopropoxy-3-pyridinyl)spiro[4.5]dec-7-ene trifluoroacetate N-Methyl-1-aza-8-(5-isopropoxy-3-pyridinyl)spiro[4.5]dec-7-ene trifluoroacetate was prepared in accordance with the following techniques:

N-Methyl-1-aza-8-(5-isopropoxy-3-pyridinyl)spiro[4.5]dec-7-ene trifluoroacetate 1-Aza-8-(5-isopropoxy-3-pyridinyl)spiro[4.5]dec-7-ene trifluoroacetate (30 mg, 0.077 mmol) was dissolved in a mixture of 98% formic acid (1 mL) and 37% aqueous formaldehyde (0.2 mL). The mixture was refluxed for 3 h, cooled and neutralized with saturated aqueous sodium bicarbonate, saturated with sodium chloride and extracted with chloroform (5×5 mL). The chloroform extracts were dried ($Na_2SO_4$) and concentrated by rotary evaporation. High-pressure liquid chromatographic purification of the residue on C18 silica gel, using a gradient of acetonitrile in water (0.1% trifluoroacetic acid), gave 22 mg (71%) of viscous, light brown oil.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

What is claimed is:

1. A compound of Formula 1:

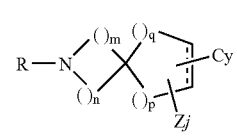

Formula I wherein:

R is H or $C_{1-10}$ alkyl;

m is 1, 2, 3, or 4;
n is 0, 1, or 2;
p is 0, 1, 2, or 3;
q is 0, 1, 2, 3, or 4; and
j is 0, 1, 2, or 3; and
the values of m, n, p and q are selected such that the depicted azaspiro ring contains 6, 7, 8, 9, 10 or 11 members; and
when m is 1, n is not 0; and
m and n combine such that the depicted aza-containing ring is 4-, 5-, or 6-membered;
each Z is, individually, selected from the group consisting of alkyl, substituted alkyl, cycloalkyl, substituted cycloalkyl, heterocyclyl, substituted heterocyclyl, aryl, substituted aryl, alkylaryl, substituted alkylaryl, arylalkyl, and substituted arylalkyl;
the dashed line represents an optional double bond;
Cy is pyridinyl or substituted pyridinyl;
wherein the term substituted refers to one or more of a group consisting of alkyl, alkenyl, heterocyclyl, cycloalkyl, aryl, alkylaryl, arylalkyl, halogen, —OR', —NR'R", —CF$_3$, —CN, —NO$_2$, —C=CR', —SR', —N$_3$, —C(=O)NR'R", —NR'C(=O) R", —C(=O)R", C(=O)OR', OC(=O)R', —O(CR'R")$_r$C(=O)R', O(CR'R")$_r$NR"C(=O)R', —O(CR'R")$_r$NR"SO$_2$R', —OC(=O)NR'R", —NR'C(=O)OR", —SO$_2$R', —SO$_2$NR'R", or —NR'SO$_2$R";
each R' and R" individually is hydrogen. C$_1$-C$_8$ alkyl, cycloalkyl, heterocyclyl, aryl, or arylalkyl and each r individually is an integer from 1 to 6; or
R' and R" can combine to form a 3- to 7-membered saturated or unsaturated ring;
or a pharmaceutically acceptable salt thereof wherein any open valences are filled by hydrogen.

2. The compound of claim 1, having one of the following formulas:

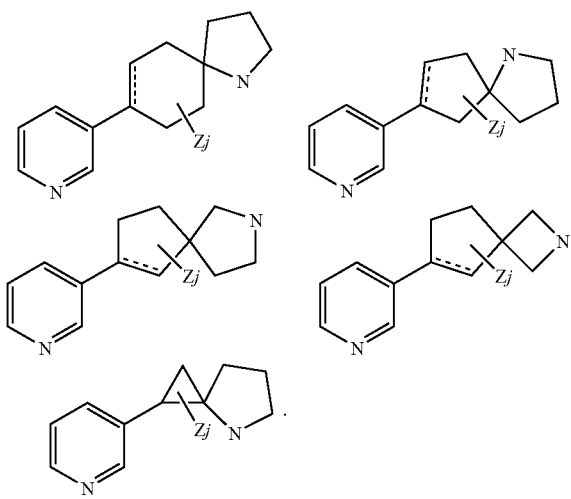

3. A pharmaceutical composition comprising a compound of claim 1 and a pharmaceutically acceptable carrier.

4. The compound of claim 1 selected from the group consisting of:
1-(3-pyridinyl)-5-azaspiro[2.3]hexane,
1-(5-methoxy-3-pyridinyl)-5-azaspiro[2.3]hexane,
1-(5-isopropoxy-3-pyridinyl)-5-azaspiro[2.3]hexane,
1-(5-cyclopentyloxy-3-pyridinyl)-5-azaspiro[2.3]hexane,
1-(5-phenoxy-3-pyridinyl)-5-azaspiro[2.3]hexane,
1-(5-(4-chlorophenoxy)-3-pyridinyl)-5-azaspiro[2.3]hexane,
1-(5-bromo-3-pyridinyl)-5-azaspiro[2.3]hexane,
1-(5-cyano-3-pyridinyl)-5-azaspiro[2.3]hexane,
1-(6-chloro-3-pyridinyl)-5-azaspiro[2.3]hexane,
1-(6-hydroxy-3-pyridinyl)-5-azaspiro[2.3]hexane,
1-(6-methoxy-3-pyridinyl)-5-azaspiro[2.3]hexane,
1-(3-pyridinyl)-4-azaspiro[2.4]heptane,
1-(5-methoxy-3-pyridinyl)-4-azaspiro[2.4]heptane,
1-(5-isopropoxy-3-pyridinyl)-4-azaspiro[2.4]heptane,
1-(5-cyclopentyloxy-3-pyridinyl)-4-azaspiro[2.4]heptane,
1-(5-phenoxy-3-pyridinyl)-4-azaspiro[2.4]heptane,
1-(5-(4-chlorophenoxy)-3-pyridinyl)-4-azaspiro[2.4]heptane,
1-(5-bromo-3-pyridinyl)-4-azaspiro[2.4]heptane,
1-(5-cyano-3-pyridinyl)-4-azaspiro[2.4]heptane,
1-(6-chloro-3-pyridinyl)-4-azaspiro[2.4]heptane,
1-(6-hydroxy-3-pyridinyl)-4-azaspiro[2.4]heptane,
1-(6-methoxy-3-pyridinyl)-4-azaspiro[2.4]heptane,
2-(3-pyridinyl)-5-azaspiro[3.4]octane,
2-(5-methoxy-3-pyridinyl)-5-azaspiro[3.4]octane,
2-(5-isopropoxy-3-pyridinyl)-5-azaspiro[3.4]octane,
2-(5-cyclopentyloxy-3-pyridinyl)-5-azaspiro[3.4]octane,
2-(5-phenoxy-3-pyridinyl)-5-azaspiro[3.4]octane,
2-(5-(4-chlorophenoxy)-3-pyridinyl)-5-azaspiro[3.4]octane,
2-(5-bromo-3-pyridinyl)-5-azaspiro[3.4]octane,
2-(5-cyano-3-pyridinyl)-5-azaspiro[3.4]octane,
2-(6-chloro-3-pyridinyl)-5-azaspiro[3.4]octane,
2-(6-hydroxy-3-pyridinyl)-5-azaspiro[3.4]octane,
2-(6-methoxy-3-pyridinyl)-5-azaspiro[3.4]octane,
6-(3-pyridinyl)-2-azaspiro[3.4]octane,
6-(5-methoxy-3-pyridinyl)-2-azaspiro[3.4]octane,
6-(5-isopropoxy-3-pyridinyl)-2-azaspiro[3.4]octane,
6-(5-cyclopentyloxy-3-pyridinyl)-2-azaspiro[3.4]octane,
6-(5-phenoxy-3-pyridinyl)-2-azaspiro[3.4]octane,
6-(5-(4-chlorophenoxy)-3-pyridinyl)-2-azaspiro[3.4]octane,
6-(5-bromo-3-pyridinyl)-2-azaspiro[3.4]octane,
6-(5-cyano-3-pyridinyl)-2-azaspiro[3.4]octane,
6-(6-chloro-3-pyridinyl)-2-azaspiro[3.4]octane,
6-(6-hydroxy-3-pyridinyl)-2-azaspiro[3.4]octane,
6-(6-methoxy-3-pyridinyl)-2-azaspiro[3.4]octane,
7-(3-pyridinyl)-2-azaspiro[4.4]nonane,
7-(5-methoxy-3-pyridinyl)-2-azaspiro[4.4]nonane,
7-(5-isopropoxy-3-pyridinyl)-2-azaspiro[4.4]nonane,
7-(5-cyclopentyloxy-3-pyridinyl)-2-azaspiro[4.4]nonane,
7-(5-phenoxy-3-pyridinyl)-2-azaspiro[4.4]nonane,
7-(5-(4-chlorophenoxy)-3-pyridinyl)-2-azaspiro[4.4]nonane,
7-(5-bromo-3-pyridinyl)-2-azaspiro[4.4]nonane,
7-(5-cyano-3-pyridinyl)-2-azaspiro[4.4]nonane,
7-(6-chloro-3-pyridinyl)-2-azaspiro[4.4]nonane,
7-(6-hydroxy-3-pyridinyl)-2-azaspiro[4.4]nonane,
7-(6-methoxy-3-pyridinyl)-2-azaspiro[4.4]nonane,
7-(3-pyridinyl)-1-azaspiro[4.4]nonane,
7-(5-methoxy-3-pyridinyl)-1-azaspiro[4.4]nonane,
7-(5-isopropoxy-3-pyridinyl)-1-azaspiro[4.4]nonane,
7-(5-cyclopentyloxy-3-pyridinyl)-1-azaspiro[4.4]nonane,
7-(5-phenoxy-3-pyridinyl)-1-azaspiro[4.4]nonane,
7-(5-(4-chlorophenoxy)-3-pyridinyl)-1-azaspiro[4.4]nonane,
7-(5-bromo-3-pyridinyl)-1-azaspiro[4.4]nonane,
7-(5-cyano-3-pyridinyl)-1-azaspiro[4.4]nonane,
7-(6-chloro-3-pyridinyl)-1-azaspiro[4.4]nonane,
7-(6-hydroxy-3-pyridinyl)-1-azaspiro[4.4]nonane, 7-(6-methoxy-3-pyridinyl)-1-azaspiro[4.4]nonane,
8-(3-pyridinyl)-1-azaspiro[4.5]decane,
8-(5-methoxy-3-pyridinyl)-1-azaspiro[4.5]decane,
8-(5-isopropoxy-3-pyridinyl)-1-azaspiro[4.5]decane,
8-(5-cyclopentyloxy-3-pyridinyl)-1-azaspiro[4.5]decane,
8-(5-phenoxy-3-pyridinyl)-1-azaspiro[4.5]decane,
8-(5-(4-chlorophenoxy)-3-pyridinyl)-1-azaspiro[4.5]decane,
8-(5-bromo-3-pyridinyl)-1-azaspiro[4.5]decane,
8-(5-cyano-3-pyridinyl)-1-azaspiro[4.5]decane,
8-(6-chloro-3-pyridinyl)-1-azaspiro[4.5 ]decane,
8-(6-hydroxy-3-pyridinyl)-1-azaspiro[4.5]decane,
8-(6-methoxy-3-pyridinyl)-1-azaspiro[4.5]decane,
2-(3-pyridinyl)-7-azaspiro[4.5]decane,
2-(5-methoxy-3-pyridinyl)-7-azaspiro[4.5]decane,
2-(5-isopropoxy-3-pyridinyl)-7-azaspiro[4.5]decane,
2-(5-cyclopentyloxy-3-pyridinyl)-7-azaspiro[4.5]decane,
2-(5-phenoxy-3-pyridinyl)-7-azaspiro[4.5]decane,
2-(5-(4-chlorophenoxy)-3-pyridinyl)-7-azaspiro[4.5]decane,
2-(5-bromo-3-pyridinyl)-7-azaspiro[4.5]decane,
2-(5-cyano-3-pyridinyl)-7-azaspiro[4.5]decane,
2-(6-chloro-3-pyridinyl)-7-azaspiro[4.5]decane,
2-(6-hydroxy-3-pyridinyl)-7-azaspiro[4.5]decane,
2-(6-methoxy-3-pyridinyl)-7-azaspiro[4.5]decane,
2-(5-pyrimidinyl)-7-azaspiro[4.5]decane,
6-(3-pyridinyl)-2-azaspiro[3.4]oct-5-ene,
6-(5-methoxy-3-pyridinyl)-2-azaspiro[3.4]oct-5-ene,
6-(5-isopropoxy-3-pyridinyl)-2-azaspiro[3.4]oct-5-ene,
6-(5-cyclopentyloxy-3-pyridinyl)-2-azaspiro[3.4]oct-5-ene,
6-(5-phenoxy-3-pyridinyl)-2-azaspiro[3.4]oct-5-ene,
6-(5-(4-chlorophenoxy)-3-pyridinyl)-2-azaspiro[3.4]oct-5-ene,
6-(5-bromo-3-pyridinyl)-2-azaspiro[3.4]oct-5-ene,
6-(5-cyano-3-pyridinyl)-2-azaspiro[3.4]oct-5-ene,
6-(6-chloro-3-pyridinyl)-2-azaspiro[3.4]oct-5-ene,
6-(6-hydroxy-3-pyridinyl)-2-azaspiro[3.4]oct-5-ene,
6-(6-methoxy-3-pyridinyl)-2-azaspiro[3.4]oct-5-ene,
7-(3-pyridinyl)-2-azaspiro[4.4]non-6-ene,
7-(5-methoxy-3-pyridinyl)-2-azaspiro[4.4]non-6-ene,
7-(5-isopropoxy-3-pyridinyl)-2-azaspiro[4.4]non-6-ene,
7-(5-cyclopentyloxy-3-pyridinyl)-2-azaspiro[4.4]non-6-ene,
7-(5-phenoxy-3-pyridinyl)-2-azaspiro[4.4]non-6-ene,
7-(5-(4-chlorophenoxy)-3-pyridinyl)-2-azaspiro[4.4]non-6-ene,
7-(5-bromo-3-pyridinyl)-2-azaspiro[4.4]non-6-ene,
7-(5-cyano-3-pyridinyl)-2-azaspiro[4.4]non-6-ene,
7-(6-chloro-3-pyridinyl)-2-azaspiro[4.4]non-6-ene,
7-(6-hydroxy-3-pyridinyl)-2-azaspiro[4.4]non-6-ene,
7-(6-methoxy-3-pyridinyl)-2-azaspiro[4.4]non-6-ene,
7-(3-pyridinyl)-1-azaspiro[4.4]non-7-ene,
7-(5-methoxy-3-pyridinyl)-1-azaspiro[4.4]non-7-ene,
7-(5-isopropoxy-3-pyridinyl)-1-azaspiro[4.4]non-7-ene,
7-(5-cyclopentyloxy-3-pyridinyl)-1-azaspiro[4.4]non-7-ene,
7-(5-phenoxy-3-pyridinyl)-1-azaspiro[4.4]non-7-ene,
7-(5-(4-chlorophenoxy)-3-pyridinyl)-1-azaspiro[4.4]non-7-ene,
7-(5-bromo-3-pyridinyl)-1-azaspiro[4.4]non-7-ene,
7-(5-cyano-3-pyridinyl)-1-azaspiro[4.4]non-7-ene,
7-(6-chloro-3-pyridinyl)-1-azaspiro[4.4]non-7-ene,
7-(6-hydroxy-3-pyridinyl)-1-azaspiro[4.4]non-7-ene,
7-(6-methoxy-3-pyridinyl)-1-azaspiro[4.4]non-7-ene,
8-(3-pyridinyl)-1-azaspiro[4.5]dec-7-ene,
8-(5-methoxy-3-pyridinyl)-1-azaspiro[4.5]dec-7-ene,
8-(5-isopropoxy-3-pyridinyl)-1-azaspiro[4.5]dec-7-ene,
8-(5-cyclopentyloxy-3-pyridinyl)-1-azaspiro[4.5]dec-7-ene,
8-(5-phenoxy-3-pyridinyl)-1-azaspiro[4.5]dec-7-ene,
8-(5-(4-chlorophenoxy)-3-pyridinyl)-1-azaspiro[4.5]dec-7-ene,
8-(5-bromo-3-pyridinyl)-1-azaspiro[4.5]dec-7-ene,
8-(5-cyano-3-pyridinyl)-1-azaspiro[4.5]dec-7-ene,
8-(6-chloro-3-pyridinyl)-1-azaspiro[4.5]dec-7-ene,
8-(6-hydroxy-3-pyridinyl)-1-azaspiro[4.5]dec-7-ene,
8-(6-methoxy-3-pyridinyl)-1-azaspiro[4.5]dec-7-ene,
2-(3-pyridinyl)-7-azaspiro[4.5]dec-1-ene,
2-(5-methoxy-3-pyridinyl)-7-azaspiro[4.5]dec-1-ene,
2-(5-isopropoxy-3-pyridinyl)-7-azaspiro[4.5]dec-1-ene,
2-(5-cyclopentyloxy-3-pyridinyl)-7-azaspiro[4.5]dec-1-ene,
2-(5-phenoxy-3-pyridinyl)-7-azaspiro[4.5]dec-1-ene,
2-(5-(4-chlorophenoxy)-3-pyridinyl)-7-azaspiro[4.5]dec-1-ene,
2-(5-bromo-3-pyridinyl)-7-azaspiro[4.5]dec-1-ene,
2-(5-cyano-3-pyridinyl)-7-azaspiro[4.5]dec-1-ene,
2-(6-chloro-3-pyridinyl)-7-azaspiro[4.5]dec-1-ene,
2-(6-hydroxy-3-pyridinyl)-7-azaspiro[4.5]dec-1-ene,
2-(6-methoxy-3-pyridinyl)-7-azaspiro[4.5]dec-1-ene,
and pharmaceutically acceptable salts thereof.

5. A pharmaceutical composition comprising a compound of claim 4 and a pharmceutically acceptable carrier.

6. The compound of claim 1 wherein R is H.

7. The compound of claim 1 wherein j is 0.

8. The compound of claim 1 wherein Cy is pyridinyl.

9. The compound of claim 1 wherein n is 0 and m is 3.

10. The compound of claim 1 wherein p is 1 or 2 and q is 1 or 2.

11. The compound of claim 1 wherein n is 0; m is 3; p is 1; and q is 2.

12. The compound of claim 1 wherein R is H; j is 0; Cy is pyridinyl; n is 0; m is 3; p is 1; and q is 2.

13. The compound of claim 12 wherein said pyridinyl is attached at the 8-position of the azaspiro ring.

14. The compound of claim 13 wherein the dashed line indicates a double bond such that the azaspiro ring is azaspirodec-7-ene.

15. The compound of claim 1 wherein Cy is pyridinyl substituted with one or more of $C_{1-6}$ alkoxy, $C_{3-6}$ cycloalkoxy, aryloxy, aryloxy substituted with one or more halogen, halogen, cyano, or hydroxyl.

16. The compound of claim 1 wherein the azaspiro ring is saturated.

17. The compound of claim 1 selected from the group consisting of:
8-(3-pyridinyl)-1-azaspiro[4.5]decane,
8-(5-methoxy-3-pyridinyl)-1-azaspiro4.5decane,
8-(5-isopropoxy-3-pyridinyl)-1-azaspirol[4.5]decane,
8-(5-cyclopentyloxy-3-pyridinyl)-1-azaspiro[4.5]decane,
8-(5-phenoxy-3-pyridinyl)-1-azaspiro[4.5]decane,
8-(5-(4-chlorophenoxy)-3-pyridinyl)-1-azaspiro[4.5]decane,
8-(5-bromo-3-pynidinyl)-1-azaspiro[4.5]decane,
8-(5-cyano-3-pyridinyl)-1-azaspiro[4.5]decane,
8-(6-chloro-3-pyridinyl)-1-azaspiro[4.5]decane,
8-(6-hydroxy-3-pyridinyl)-1-azaspiro[4.5]decane,
8-(6-methoxy-3-pyridinyl)-1-azaspiro4.5decane,
2-(3-pyridinyl)-7-azaspiro[4.5]decane,
8-(3-pyridinyl)-1-azaspiro[4.5]dec-7-ene,
8-(5-methoxy-3-pyridinyl)-1-azaspiro[4.5]dec-7-ene,
8-(5-isopropoxy-3-pyridinyl)-1-azaspiro[4.5]dec-7-ene, 8-(5-cyclopentyloxy-3-pyridinyl)-1-azaspiro[4.5]dec-7-ene,
8-(5-phenoxy-3-pyridinyl)-1-azaspiro[4.5]dec-7-ene,
8-(5-(4-chlorophenoxy)-3-pyridinyl)-1-azaspiro4.5dec-7-ene,
8-(5-bromo-3-pyridinyl)-1-azaspiro4.5dec-7-ene,
8-(5-cyano-3-pyridinyl)-1-azaspiro[4.5]dec-7-ene,
8-(6-chloro-3-pyridinyl)-1-azaspiro[4.5]dec-7-ene,
8-(6-hydroxy-3-pyridinyl)-1-azaspiro4.5dec-7-ene,
8-(6-methoxy-3-pyridinyl)-1-azaspiro[4.5]dec-7-ene,
and pharmaceutically acceptable salts thereof.

18. The compound of claim 1 selected from the group consisting of:
1-(3-pyridinyl)-5-azaspiro[2.3]hexane,
1-(3-pyridinyl)-4-azaspiro[2.4]heptane,
2-(3-pyridinyl)-5-azaspiro[3.4]octane,
6-(3-pyridinyl)-2-azaspiro[3.4]octane,
7-(3-pyridinyl)-2-azaspiro[4.4]nonane,
7-(3-pyridinyl)-1-azaspiro[4.4]nonane,
8-(3-pyridinyl)-1-azaspiro4.5decane,
2-(3-pyridinyl)-7-azaspiro[4.5]decane,
6-(3-pyridinyl)-2-azaspiro[3.4]oct-5-ene,
7-(3-pyridinyl)-2-azaspiro[4.4]non-6-ene,
7-(3-pyridinyl)-1-azaspiro[4.4]non-7-ene,
8-(3-pyridinyl)-1-azaspiro[4.5]dec-7-ene,
2-(3-pyridinyl)-7-azaspiro[4.5]dec-1-ene,
and pharmaceutically acceptable salts thereof.

19. A compound 8-(3-pyridinyl)-1-azaspiro[4.5]dec-7-ene or a pharmaceutically acceptable salt thereof.

20. A pharmaceutical composition comprising 8-(3-pyridinyl)-1-azaspiro[4.5]dec-7-ene or a pharmaceutically acceptable salt thereof and a pharmceutically acceptable carrier.

* * * * *

UNITED STATES PATENT AND TRADEMARK OFFICE
CERTIFICATE OF CORRECTION

PATENT NO.        : 7,384,929 B2                                             Page 1 of 3
APPLICATION NO.   : 11/230140
DATED             : June 10, 2008
INVENTOR(S)       : Bhatti et al.

It is certified that error appears in the above-identified patent and that said Letters Patent is hereby corrected as shown below:

On page 2, column 1, under OTHER PUBLICATIONS, lines 31 and 34, the word "Americ" should be --Arneric--

In the Specification:

Column 2, line 59, the phrase "exhibitnicotinic" should be --exhibit nicotinic--

Column 5, line 45, the word "constanta" should be --constants--

Column 6, line 21, phrase "values of m, n, p and l" should be --values of m, n, p, and q--

Column 6, line 45, the structure needs another double bond (between X'''' and X'''')

Column 8, line 13, "x'" should be --X'--

Column 17, line 39, Scheme III, error in the formula should be corrected as shown below:

" 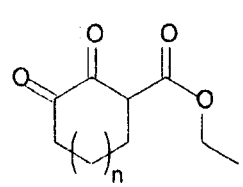 " should be -- 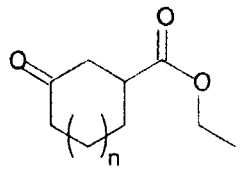 --

In the Claims:

Claim 1, column 35, line 6 "the values of m, n, p and q" should be --the values of m, n, p, and q--

Signed and Sealed this

Twenty-seventh Day of July, 2010

David J. Kappos
*Director of the United States Patent and Trademark Office*

CERTIFICATE OF CORRECTION (continued)
U.S. Pat. No. 7,384,929 B2

Claim 1, column 35, line 7 "depicted azaspiro ring contains 6, 7, 8, 9, 10 or 11" should be --depicted azaspiro ring contains 6, 7, 8, 9, 10, or 11--

Claim 1, Column 35, line 22 "-C=CR'," should be -- -C≡CR'--

Claim 1, Column 35, line 24 "R", C(=O)OR', OC" should be --R',-C(=O)OR',-OC--

Claim 1, Column 35, line 25 "O(CR'R")$_r$" should be -- -O(CR'R")$_r$--

Claim 1, Column 35, "is hydrogen." should be --is hydrogen,--

Claim 2, Column 35, line 55 "or" is missing in the formulae as follows:

CERTIFICATE OF CORRECTION (continued)
U.S. Pat. No. 7,384,929 B2

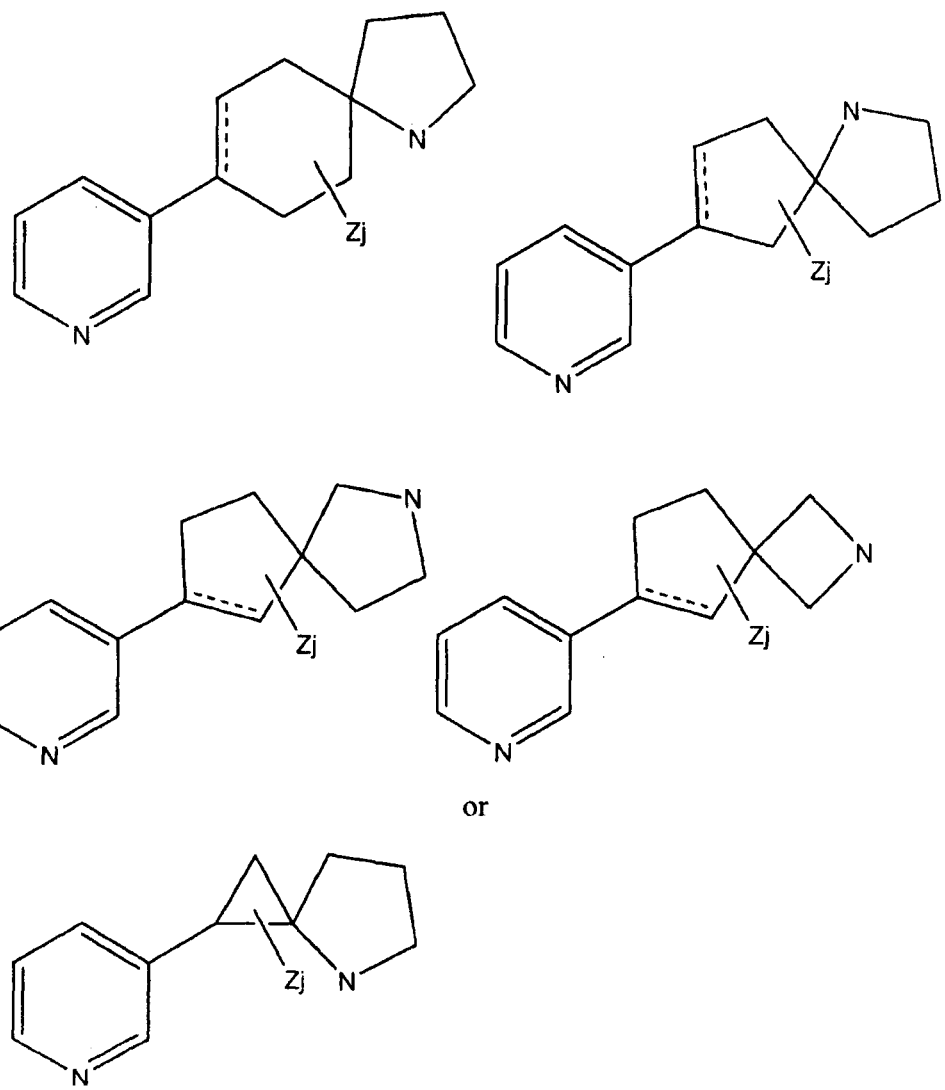

or

Claim 4, Column 37, line 26 "2-(5-pyrimidinyl)-7-azaspiro[4.5] decane," should be deleted.

Claim 4, Column 38, line 25 "and pharmaceutically acceptable salts thereof." should be --or a pharmaceutically acceptable salt thereof--

Claim 17, Column 38, line 59 "(5-bromo-3-pynidinyl)" should be --(5-bromo-3-pyridinyl)--

Claim 17, Column 39, line 4 "-1-azaspiro4.5dec-7-" should be -- -1-azaspiro[4.5]dec-7-ene,--

Claim 17, Column 39, line 6 "-1-azaspiro4.5dec-7-" should be -- -1-azaspiro[4.5]dec-7-ene,--